(12) United States Patent
Scheib

(10) Patent No.: US 11,076,883 B2
(45) Date of Patent: Aug. 3, 2021

(54) CANNULA ATTACHMENT DEVICES AND METHODS FOR A SURGICAL ROBOTIC SYSTEM

(71) Applicant: Verb Surgical Inc., Mountain View, CA (US)

(72) Inventor: Charles J Scheib, Loveland, OH (US)

(73) Assignee: VERB SURGICAL INC., Santa Clara, CA (US)

( * ) Notice: Subject to any disclaimer, the term of this patent is extended or adjusted under 35 U.S.C. 154(b) by 246 days.

(21) Appl. No.: 15/999,399

(22) Filed: Aug. 20, 2018

(65) Prior Publication Data

US 2019/0053824 A1 Feb. 21, 2019

Related U.S. Application Data

(60) Provisional application No. 62/548,292, filed on Aug. 21, 2017.

(51) Int. Cl.
*A61B 17/34* (2006.01)
*A61B 34/30* (2016.01)
(Continued)

(52) U.S. Cl.
CPC ...... *A61B 17/3421* (2013.01); *A61B 17/3476* (2013.01); *A61B 34/30* (2016.02);
(Continued)

(58) Field of Classification Search
None
See application file for complete search history.

(56) References Cited

U.S. PATENT DOCUMENTS

| 7,314,331 B1 * | 1/2008 | Koros | A61B 90/57 403/385 |
|---|---|---|---|
| 8,182,469 B2 | 5/2012 | Anderson et al. | |

(Continued)

FOREIGN PATENT DOCUMENTS

| JP | 2012254360 A | 12/2012 |
|---|---|---|
| JP | 2017513552 A | 6/2017 |

OTHER PUBLICATIONS

International Preliminary Report on Patentability for International Application No. PCT/US2018/047388, dated Mar. 5, 2020, 8 pages.

(Continued)

*Primary Examiner* — Shaun L David
(74) *Attorney, Agent, or Firm* — Womble Bond Dickinson (US) LLP

(57) ABSTRACT

A robotic surgical system may include a cannula attachment device or cannula mount having a locking mechanism configured to pivot between an unlocked position and a locked over-center position. The locking mechanism may actuate a clamp or other feature that is configured to move between a closed position and an open position. The clamp may include a locating structure with one or more tapered surfaces that is configured to mate with a corresponding structure disposed on a portion of a cannula when the cannula is positioned in the cannula attachment device. The locating structure may guide the cannula into the attachment device, as well as assist with orientating the cannula relative to the attachment device.

20 Claims, 18 Drawing Sheets

(51) Int. Cl.
*A61B 90/57* (2016.01)
*A61B 34/00* (2016.01)
*A61B 17/00* (2006.01)
*A61B 90/50* (2016.01)

(52) U.S. Cl.
CPC .............. *A61B 34/70* (2016.02); *A61B 90/57* (2016.02); *A61B 90/50* (2016.02); *A61B 2017/00477* (2013.01); *A61B 2017/347* (2013.01)

(56) References Cited

U.S. PATENT DOCUMENTS

| | | | |
|---|---|---|---|
| 2006/0161136 A1* | 7/2006 | Anderson | A61B 90/57 606/1 |
| 2015/0133958 A1* | 5/2015 | Singh | A61B 17/4241 606/130 |
| 2016/0242861 A1 | 8/2016 | Flatt | |
| 2017/0086930 A1 | 3/2017 | Thompson | |

OTHER PUBLICATIONS

International Search Report and Written Opinion dated Dec. 13, 2018, for related Japanese Appln. No. PCT/US2018/047388 13 Pages.

Examination Report for Australian Application No. 2018321328 dated May 12, 2020, 5 pages.

Japanese Office Action from related Application No. JP 2020-506993 dated Feb. 24, 2021 (9 pages including English translation).

* cited by examiner

CANNULA ATTACHMENT DEVICES AND METHODS FOR A SURGICAL ROBOTIC SYSTEM

CROSS-REFERENCE AND RELATED APPLICATIONS

This application claims priority to U.S. Provisional Patent Application Ser. No. 62/548,292, filed Aug. 21, 2017, which is hereby incorporated by reference in its entirety.

TECHNICAL FIELD

This invention relates generally to robotic surgical systems, and more specifically to new and useful attachment devices and methods for attaching a sterile component to one or more non-sterile components of a robotic surgical system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

During a robotic MIS, a surgeon or other operator may use a number of different surgical instruments to perform a procedure at a surgical site. Oftentimes, a surgeon may rely on the use of a trocar or a cannula to target a site within a patient's body. The cannula may provide a channel or opening through which additional surgical instruments may be introduced and removed by a surgeon. For example, a cannula can be positioned within a patient in a body cavity, and a surgical instrument can be inserted into the cannula and guided to the body cavity via the cannula. In a robotic system, the cannula may be mounted to one or more robotic arms, which may be remotely controlled by the surgeon to move the cannula. A cannula mount may be used to attach the cannula to a robotic arm to ensure proper control and placement of the cannula within the patient. Many conventional cannula mounts, however, are small in size and limited in how much load they can carry. These cannula mounts may use complex latching systems to secure a cannula in place relative to a robotic arm, but they may be difficult to use and sensitive to variation in cannula dimensions. Similar to traditional surgical procedures, it is also important to maintain a sterile environment in the surgical field during robotic MIS. In view of these areas for improvement, it is desirable to have new and improved cannula mounts and attachment methods in a robotic surgical system.

SUMMARY

Generally, in some variations, a robotic surgical system may include an apparatus for attaching a cannula to the surgical system. The apparatus may have a first clamp component and a second clamp component spaced apart from each other. The first clamp component may be configured to pivot between an open position and a closed position. The first and second clamp components may define a region for receiving a portion of a cannula. When the first clamp component is in the closed position, the first and second clamp components may retain the portion of the cannula within the region between the first and second clamp components. The apparatus may further have a locking component that is coupled to the first clamp component and configured to pivot the first claim component between the open position and the closed position. Additionally or alternatively, the locking component may be coupled to the second clamp component.

In some variations, the locking component may be pivotable between an unlocked position and a locked position. The locked position may, for example, be a locked over-center position. When the locking component is in the unlocked position, the first clamp component may be in the open position, and when the locking component is in the locked position, the first clamp component may be in the closed position. The locking component may be configured to lock the first clamp component in the closed position when the locking component is in the locked position. For example, the locking component can be biased toward the locked position when the locking component is in the locked position. In some variations, the robotic surgical system and/or the attachment apparatus may include a spring configured to bias the first clamp component in the closed position.

In some variations, the first clamp component may have a slot that extends along a partial length of the first clamp component. A first end of the locking component may be disposed in and moveable along a length of the slot of the first clamp component, and a second end of the locking component may be moveable to pivot the locking component between the unlocked position and the locked over-center position. The first end of the locking component may move in a first direction along the slot when the locking component pivots from the unlocked position to the locked over-center position, and the first end of the locking component can move in a second direction along the slot opposite to the first direction when the locking component pivots from the locked over-center position to the unlocked position.

In some variations, at least one of the first clamp component and the second clamp component may include a locating structure configured to mate with a corresponding structure disposed on the portion of the cannula. The locating structure may be configured to guide the portion of the cannula into the region between the first and second clamp components in a predefined orientation relative to the first and second clamp components. In some variations, the locating structure includes a first tapered surface and a second tapered surface, where the two tapered surfaces form a triangular protrusion. The triangular protrusion may be configured to latch into the portion of the cannula and retain the portion of the cannula within the region defined by the first and second clamp components when the first clamp component is in the closed position. In other variations, the locating structure can be other suitable shapes, such as generally frusto-pyramidal.

In some variations, the robotic surgical system and/or the attachment apparatus may also include a sterile barrier that separates the first and second clamp components of the attachment apparatus from the cannula. The sterile barrier may separate non-sterile components of the surgical system, such as the first and second clamp components, from sterile components of the surgical system, including the cannula.

In some variations, a method may include positioning a locking component of an attachment apparatus for a cannula in an unlocked position, inserting a portion of the cannula into a region between a first clamp component and a second clamp component, and moving the locking component from the unlocked position to a locked over-center position. The locking component may be operatively coupled to the first clamp component and configured to pivot the first clamp component between an open position and a closed position; therefore, moving the locking component from the unlocked position to a locked over-center position may pivot the first clamp component to the closed position such that the first and second clamp components are configured to retain the portion of the cannula in the region between the first and second clamp components.

BRIEF DESCRIPTION OF THE DRAWINGS

FIG. 7A depicts the cannula attachment device in a first configuration, and FIG. 7B depicts the cannula attachment device in a second configuration.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Figure 1:
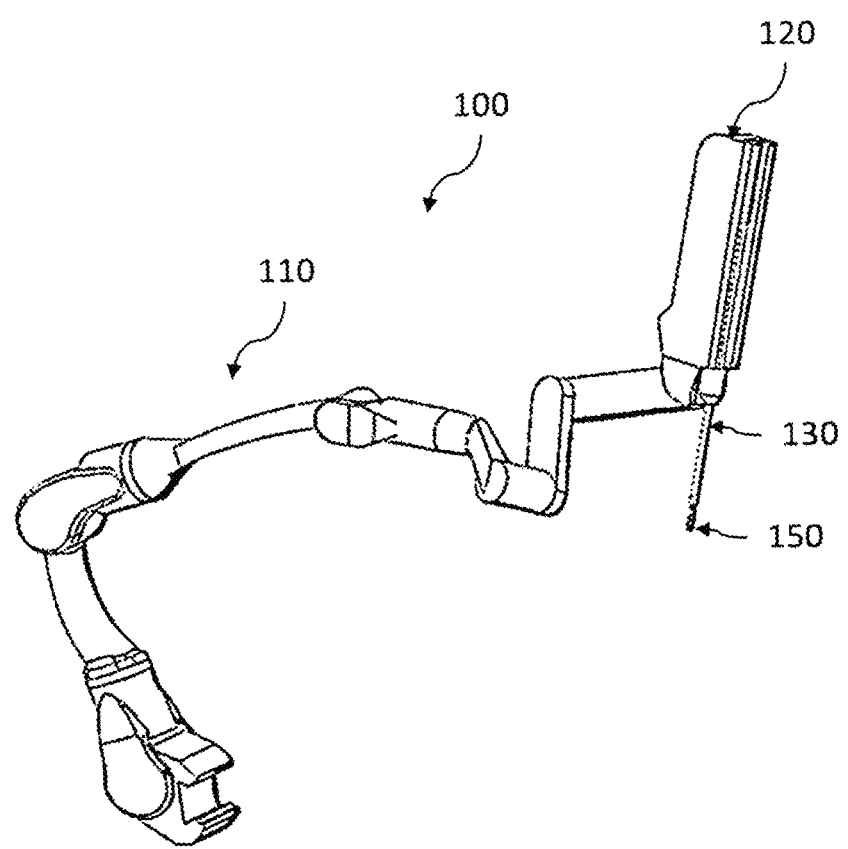
FIG. 1 is a schematic illustration of an exemplary variation of a cannula and a surgical instrument coupled to a robotic arm.

Generally, a robotic or robotic-assisted surgical system (e.g., to enable a minimally-invasive surgical procedure) may include one or more robotic arms for manipulating surgical instruments, such as during minimally-invasive surgery. For example, as shown in the exemplary schematic of FIG. 1, a portion of a robotic surgical system 100 may include a robotic arm 110 and an instrument driver or actuator 120 generally attached to a distal end of the robotic arm 110. A cannula 130 may be coupled to the instrument driver 120 or a portion of the robotic arm 110 disposed proximate to the instrument driver 120. The cannula 130 may have a lumen through which a surgical instrument 150 may be received. Furthermore, the robotic arm 110 may include a plurality of links that are actuated so as to position and orient the instrument driver 120, the cannula 130, and/or the surgical instrument 150 relative to a patient's body.

For use in a surgical procedure, the robotic arm 110 may be mounted to an operating table on which a patient lies (or on a cart, ceiling, sidewall, etc. near the patient). To create a port for enabling introduction of a surgical instrument into the patient, a trocar assembly may be at least partially inserted into the patient through an incision or entry point in the patient (e.g., in the abdominal wall). The trocar assembly may include the cannula 130, an obturator, and/or a seal. In some variations, the trocar assembly can include an obturator such as a needle with a sharpened tip for penetrating through a patient's skin. The obturator may be disposed within the lumen of the cannula 130 when being inserted into the patient, and then removed from the cannula 130 such that a surgical instrument may be inserted through the lumen of the cannula 130. Once positioned within the patient's body, the cannula 130 may provide a channel for accessing a body cavity or other site within the patient. When a surgical instrument such as the surgical instrument 150 is coupled to the instrument driver 120, the surgical instrument 150 may be disposed within the cannula 130 and extend through the lumen of the cannula 130 such that a portion of the surgical instrument 150 (e.g., an instrument shaft) passes through the cannula 130 into the patient. The instrument 150 may have an end effector disposed at the distal end of the instrument shaft, and the instrument driver 120 may further be controlled to position and/or actuate one or more degrees of freedom of the instrument 150 to perform various tasks during a surgical procedure (e.g., cutting, grasping, etc.) in accordance with the particular kind of end effector. Additionally, the instrument 150 may be withdrawn from the port (and withdrawn from the cannula 130) and decoupled from the instrument driver 120 to exchange with another instrument, such as another instrument having an end effector with different functionality.

Over-Center Variations

In some variations, the cannula 130 may be coupled to instrument driver 120 or another component of the surgical system using a cannula attachment device or a cannula mount. The attachment device may provide a reliable and quick way to attach the cannula 130 to the surgical system. In some variations, the attachment device may include first and second clamp components (e.g., arms, plates, levers, members) that can define a region for receiving a portion of a cannula (e.g., an attachment portion of a cannula located in a proximal portion of the cannula). At least one of the clamp components may be pivotable between an open position such that the cannula can be inserted into the region between the clamp components and a closed position such that the cannula is held in place at least partially by the first and second clamp components.

Figure 2A:
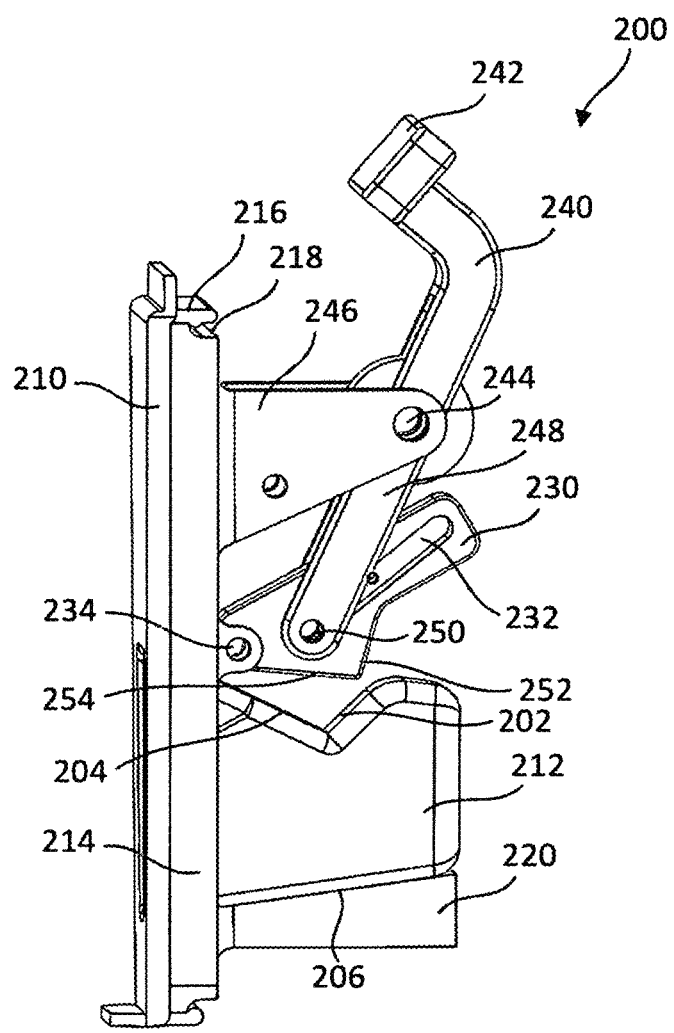
FIG. 2A is a perspective view of an exemplary variation of a cannula attachment device or cannula mount.
Figure 2B:
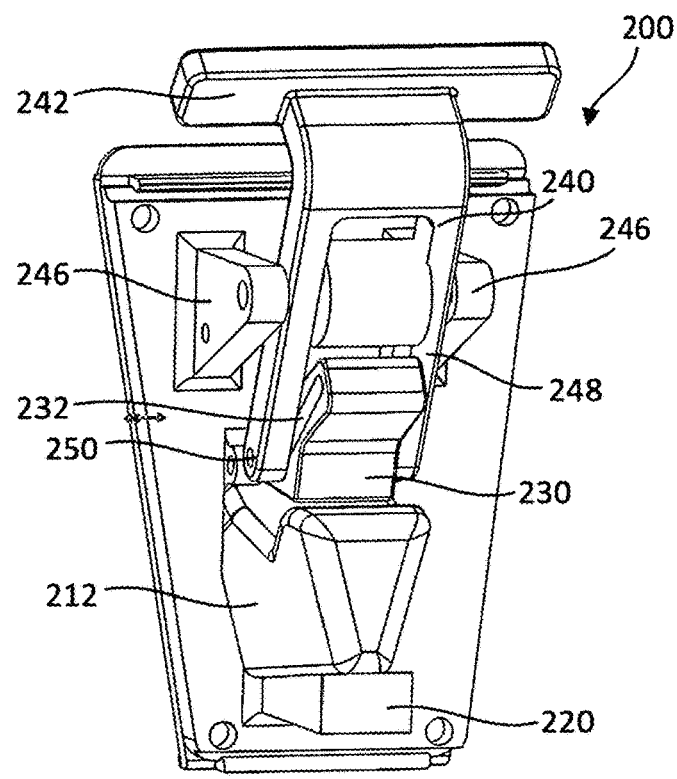
FIG. 2B is another perspective view of the cannula attachment device depicted in FIG. 2A, as shown from a different perspective.
Figure 2C:
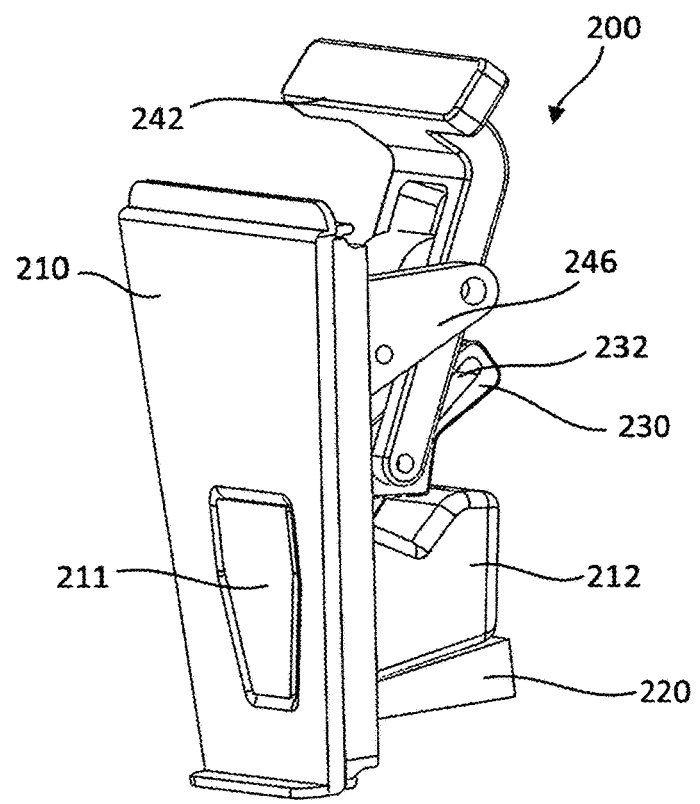
FIG. 2C is another perspective view of the cannula attachment device depicted in FIG. 2A, as shown from a different perspective.

As shown in, for example, FIGS. 2A-2C, the attachment device may include an over-center mechanism such as a lever or other suitable locking component 240 that is configured to pivot a pivotable clamp component 230 between the open and closed positions. The over-center mechanism may, for example, help lock clamp components 220, 230 together around a portion of the cannula, thereby securing the cannula to the cannula attachment device. The lever can be movable between an unlocked position and a locked position (e.g., a locked over-center position). When the lever is in the locked position, the lever may lock the pivotable clamp component 230 in the closed position such that the cannula is securely held between the first and second clamp components. In some variations, the lever may have a first end with a peg that is located in a slot 232 on the pivotable clamp component (or the lever may engage with the pivotable clamp component in any suitable manner) and a second end with one or more user contact points 242 (e.g., a handle or knob). The lever may be pivotable about a point disposed between its first and second ends. A user may apply a force to the contact point (e.g., press on the contact point) to effect translation of the peg of the lever in the slot. For example, in the locked position, the peg of the lever may be translated to a position that is over-center relative to the pivot point of the lever. In the over-center position, the peg resists movement back toward its initial position, thereby reducing the risk of the lever moving and releasing the pivotable clamp component from engagement with the cannula. In some variations, the attachment device may include a spring or other biasing element that is configured to bias the lever in the locked over-center position.

In some variations, the cannula attachment device may have at least one locating structure that may, for example, help align and position the cannula relative to one or more of the clamp components in a consistent, pre-defined manner. For example, as shown in FIG. 2A, at least one of the clamp components may have one or more protrusions (e.g., surfaces 252, 254 on the clamp component 230) shaped to mate with a correspondingly-shaped recess disposed on a portion of the cannula (e.g., an attachment portion of the cannula). For example, the protrusion may be generally frusto-pyramidal (e.g., four-sided sloped structure) that may be inserted into or otherwise engage with a recess on a proximal portion of the cannula when the proximal portion of the cannula is inserted into the region between the first and second clamp components in a specific, predefined orientation. Once the first and second clamp components 220, 230 close around the portion of the cannula (e.g., when the pivotable clamp component is in the closed position), the protrusion may be seated in the recess disposed on the portion of the cannula. In some variations, the protrusion on the clamp component may have a deep pull-back angled surface that resists the portion of the cannula from being removed from the region between the first and second clamp components when the first and second clamp components have closed around the portion of the cannula. In other variations, the locating structure may be a two-sided ramp or have two sloped surfaces that form a triangular protrusion, or have any suitable shape. Similar to the pyramid, the two-sided ramp may be shaped to engage with a correspondingly-shaped recess (e.g., triangular cutout) disposed on a portion of the cannula. In still other variations, one or more of the clamp components may additionally or alternatively include at least one locating structure that is a recess shaped to engage with a protrusion disposed on a portion of the cannula.

In some variations, a first clamp component may be moveable or pivotable between an open position and a closed position, such as described above, and a second clamp component may be stationary or fixed. In these variations, the locating structure (e.g., a pyramid, a two-sided ramp, etc.) may be located on the first, moveable clamp component or on the second, fixed clamp component. In other variations, each of the first and second clamp components may have a locating structure such as a sloped surface, a projection, or a recess. In some variations, one of the clamp components may have a surface providing a back angle that prevents the portion of the cannula received between the first and second clamp components from being removed or disengaged from the first and second clamp components.

In some variations, the attachment device may also provide a sterile barrier between sterile components such as the cannula and non-sterile components such as the first and second clamp components (or other non-sterile components of the surgical system). The sterile barrier may be provided, for example, by a sterile adapter that is interposed between the cannula and the first and second clamp components.

In some variations, the attachment device may have sensing capabilities for sensing and/or identifying a trocar or cannula. For example, the attachment device may have a sensor (e.g., a magnetic, electric, and/or optic sensor, etc.) that detects a position of the latch of the cam lock mechanism in order to determine whether the latch has latched onto a cannula or trocar. As another example, the attachment device may have a sensor that determines a type of trocar or cannula that has been inserted into the attachment device.

Figure 4A:
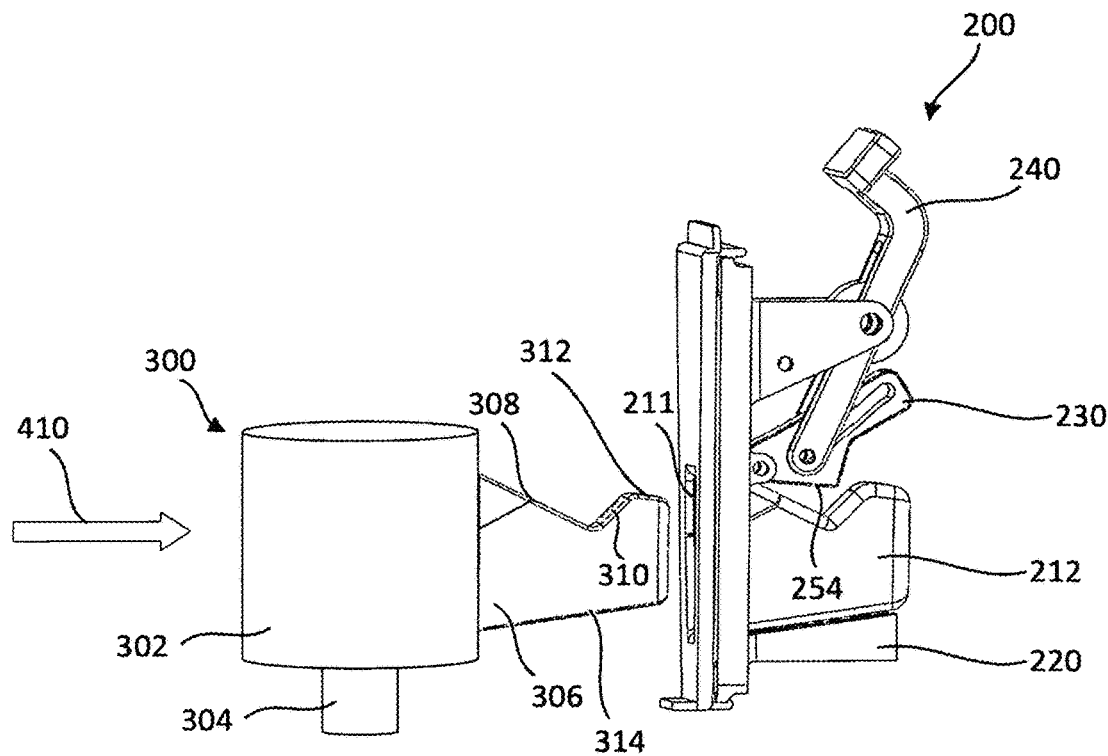
FIG. 4A is a perspective view of the cannula attachment system depicted in FIG. 3 with the sterile barrier engaged with the cannula attachment device.
Figure 4B:
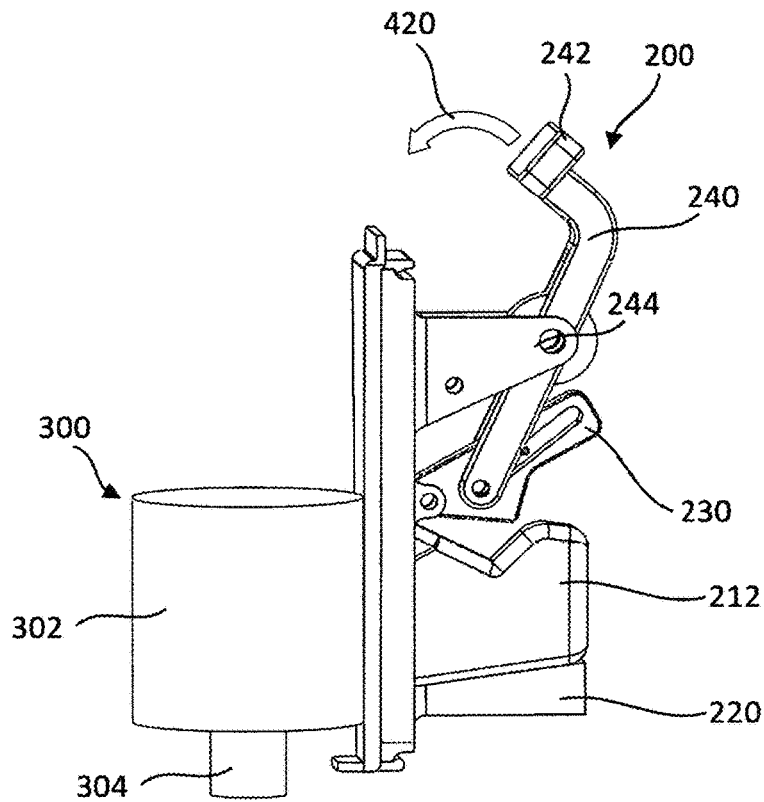
FIG. 4B is a perspective view of the cannula attachment system depicted in FIG. 3 with a portion of the cannula inserted within the cannula attachment device.
Figure 5C:
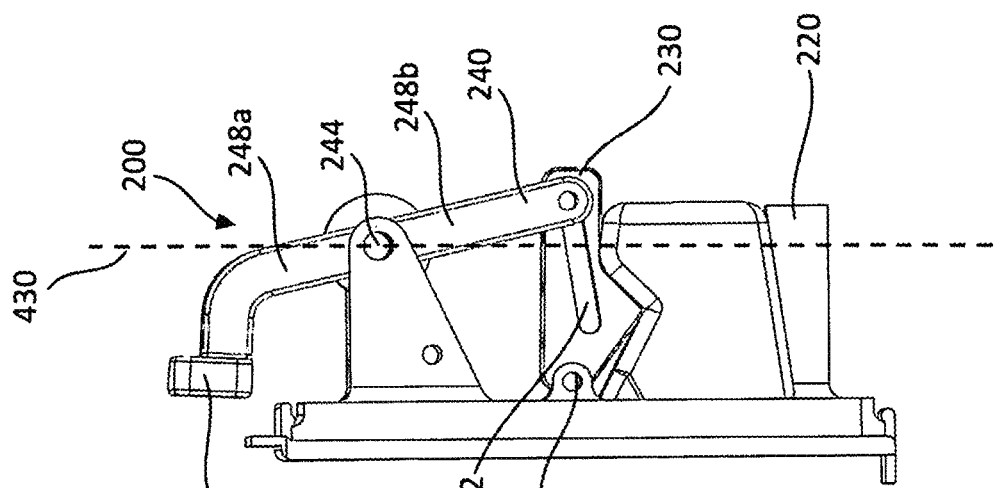
FIGS. 5A, 5B, and 5C depict the cannula attachment device of FIG. 2A in three different configurations.
Figure 5B:
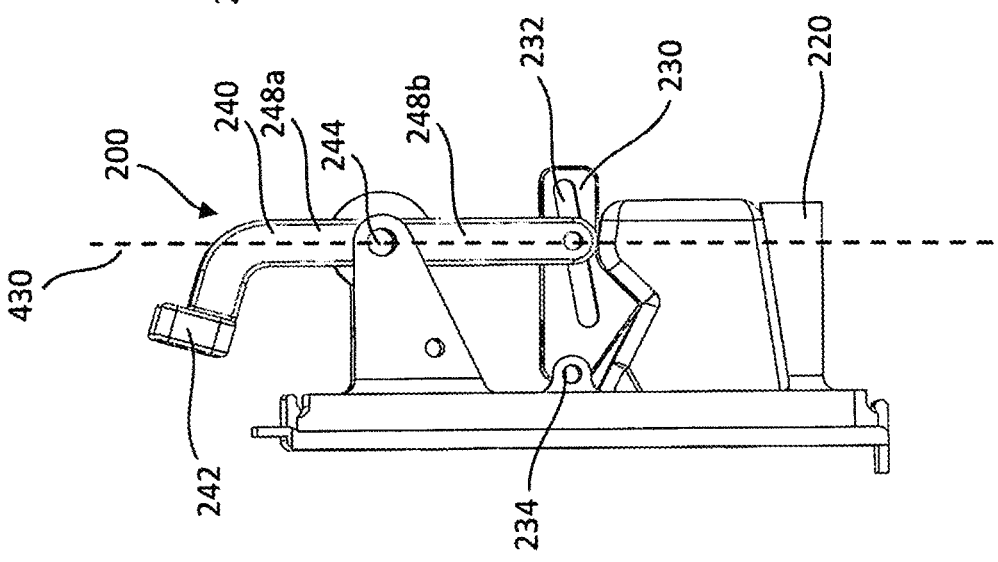
Figure 5A:
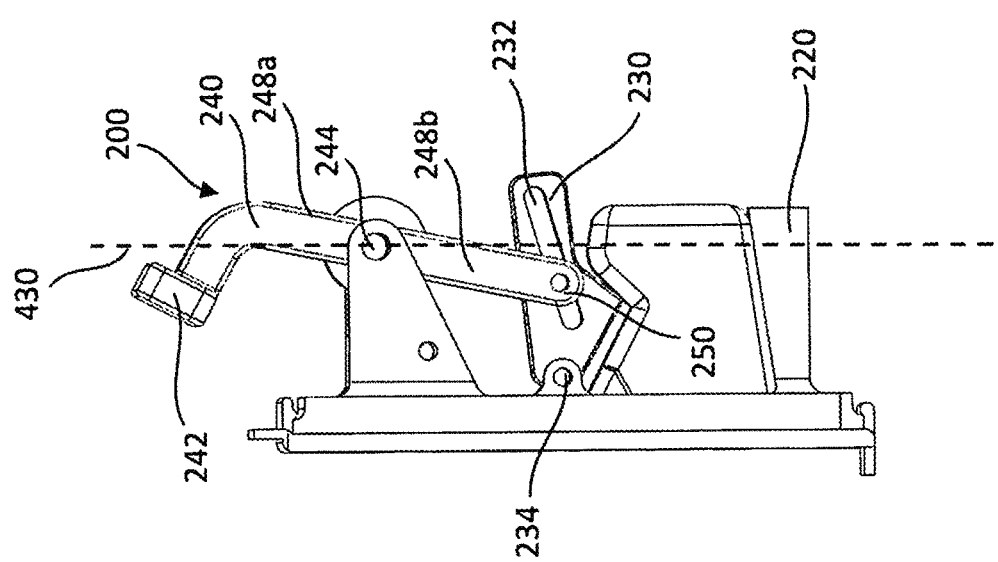
Figure 6:
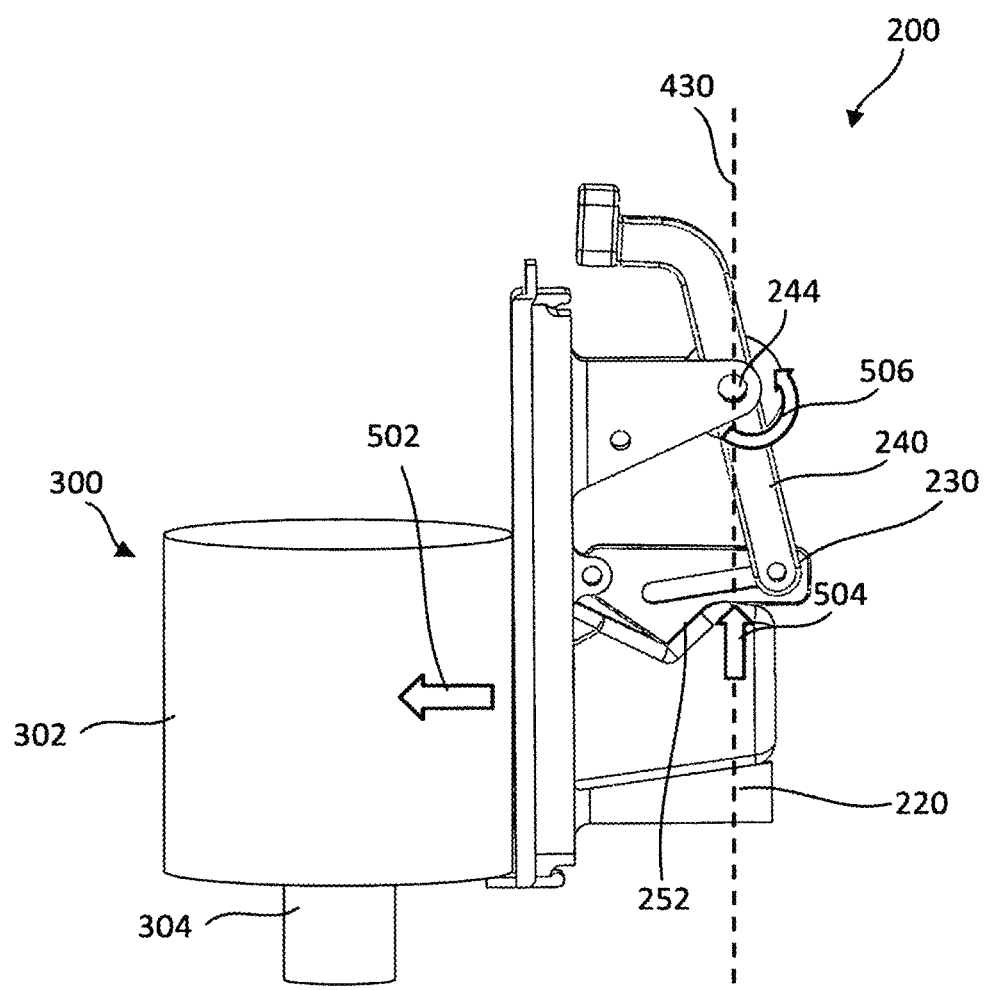
FIG. 6 depicts an over-center arrangement of the cannula attachment device of FIG. 2A.

FIGS. 2A-6 depict an exemplary variation of an attachment device for mounting a cannula, such as a cannula 300, having two clamp components. FIGS. 2A-2C depict different views of the attachment device 200. As shown in FIGS. 2A-2C, the attachment device 200 may have a first clamp component 230 that is moveable or pivotable about a first pivot point 234. The first clamp component 230 may pivot about the first pivot point 234 between an open position, such as is shown in FIGS. 2A-2C and 4A-4B, and a closed position, such as is shown in FIGS. 5C and 6. The attachment device 200 may also have a second clamp component 220. In some variations, the second clamp component 220 may be fixed or stationary. In other variations, the second clamp component 220 may be pivotable similar to the first clamp component. The second clamp component 220 may be spaced from the first clamp component such that the two clamp components 220, 230 define a region between them that is configured to receive a portion of the cannula 300 such as, for example, an attachment portion 306 of the cannula 300 (see FIG. 3). The two clamp components 220, 230 may be supported on a support component 214 such as, for example, a plate, bar, beam, or other suitable surface of a tool driver in a robotic surgical system. The first clamp component 230 may be supported on the support component 214 at a first location via the first pivot point 234 (e.g., pin joint, hinge, etc.), and the second clamp component 220 may be supported on the support component 214 at a second location spaced from the first clamp component 230. In some variations, the first clamp component 230 can be attached to a pivoting structure that allows the first clamp component 230 to rotate about the pivot point 234, and the pivoting structure can be attached to the support component 214. In such variations, the first clamp component 230 can be attached to the pivoting structure via a fastener (e.g., bolt, nail, screw, pin, etc.) or an adhesive (e.g., epoxies, polyurethanes, polyimides, etc.), and/or via other fastening techniques including, for example, crimping, welding, brazing, etc. In other variations, the first clamp component 230 can be integrally formed with a pivoting structure such as, for example, a living hinge. In some variations, the second clamp component 220 can be directly attached to the support component 214 via a fastener (e.g., bolt, nail, screw, pin, etc.), an adhesive (e.g., epoxies, polyurethanes, polyimides, etc.), and/or other fastening technique (e.g., crimping, welding, brazing, etc.). In other variations, the second clamp component 220 can be integrally formed with the support component 214. In some variations, the two clamp components 220, 230 can be formed of a plastic, a metal, or a composite material. In some variations, the two clamp components 220, 230 can be formed via machining, molding, or other manufacturing techniques.

Although the variation shown in FIGS. 2A-6 generally depict two opposing clamp components, it should be understood that in other variations, the attachment device may include more than two clamp components. For example, at least two clamp components may be pivoting simultaneously in parallel to clamp onto a first side of the cannula (e.g., two clamp components moving similar to the pivotable clamp component 230 described above), and/or at least two clamp components may be included to clamp onto a second side of the cannula (e.g., two prong-like clamp components fixed similar to the second clamp component 220 described above). In some variations, more than two clamp components may border an attachment region for receiving the cannula on different sides, and each clamp component may be separately actuated by a user to close around the cannula when the cannula is received in the attachment region. For example, two clamp components 220, 230 can border a first and second side of an attachment region for receiving the cannula, such as shown in FIGS. 2A-6, and two additional clamp components can border a third and a fourth side of the attachment region. The two additional clamp components may be separately actuated by a user to close around the cannula (e.g., a user can clamp the two clamp components 220, 230 around the cannula, and then clamp the additional clamp components around the cannula), or the two additional clamp components may be actuated together with the two clamp components 220, 230 using a single actuation mechanism. In some variations, one or more outer clamp components (or other fastening mechanisms) may also be disposed around one or more inner clamp components such that the outer clamp components can close around the inner clamp components to further secure the engagement between the inner clamp components and the cannula.

Figure 3:
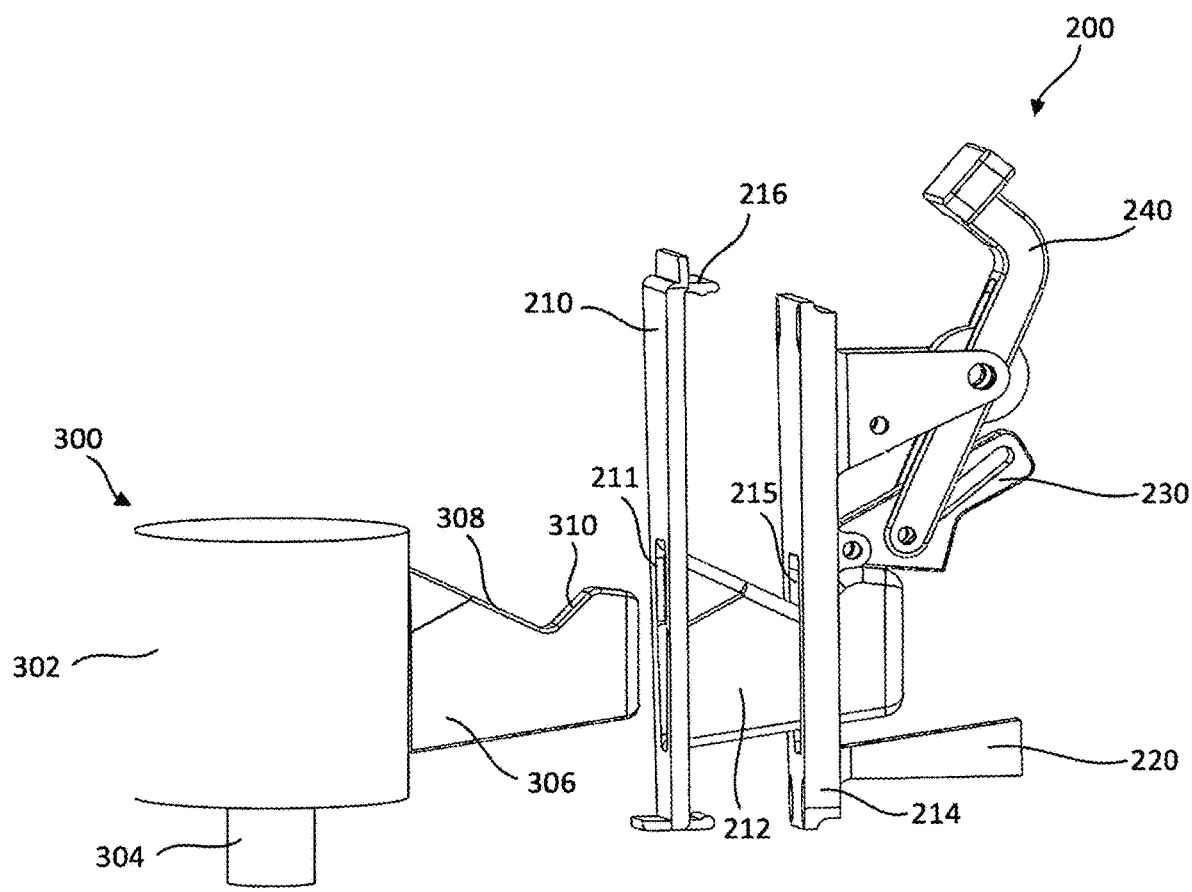
FIG. 3 is an exploded view of an exemplary variation of a cannula attachment system, including a cannula, a sterile barrier, and the cannula attachment device depicted in FIG. 2.

As shown in FIG. 3, the cannula 300 may have a proximal portion 302, such as, for example, a hub, fitting, connector, etc. The proximal portion 302 of the cannula 300 may include the attachment portion 306. The attachment portion 306 may extend from a side of the proximal portion 302. The cannula 300 may also have a shaft 304 (partially depicted in FIG. 3) that extends from the proximal portion 302. The shaft 304 may have a lumen through which one or more surgical instruments may be inserted. When the cannula 300 is disposed in a patient, a distal end of the shaft may be positioned within the patient's body such as, for example, in a body cavity.

The attachment device 200 may also have a locking component 240 such as, for example, a lever. The locking component 240 may be moveably coupled to the first clamp component 230 and configured to move or pivot about a second pivot point 244. As depicted in FIGS. 2A-2C, the second pivot point 244 may be disposed between two ends of the locking component 240. The pivot point 244 may be supported on a structure including two plates 246 that are coupled to the support component 214. The two plates 246 may include or be coupled to a bolt, pin, or other structure that fits into one or more openings formed in the locking component 240. Alternatively, the two plates 246 may include openings through which a bolt, pin, or other structure coupled to the locking component 240 may fit. The engagement between the bolt, pin, or other structure and the locking component 240 may allow the locking component 240 to rotate or pivot. The locking component 240 may be pivotable about the second pivot point 244 between an unlocked position, as shown in FIGS. 2A-2C and 4A-4B, and a locked over-center position, as shown in FIGS. 5C and 6. When the locking component 240 is in the unlocked position, the first clamp component 230 is in the open position, and when the locking component 240 is in the locked over-center position, the first clamp component 230 is in the closed position.

The attachment device 200 may include at least one locking feature or locating structure configured to mate with a corresponding structure disposed on a portion of the cannula 300, such as for example, the attachment portion 306 of the cannula 300. In some variations, the locating structure can be disposed on the first clamp component 230. Additionally or alternatively, the locating structure can be at least partially disposed on the second clamp component 220, or another component or surface adjacent to or surrounding the region between the two clamp components 220, 230. In the variation depicted in FIG. 2A, the locating structure is located on the first clamp component 230 and may be formed from two surfaces 252, 254. The two surfaces 252, 254 may be tapered surfaces that form a triangular protrusion or a two-sided ramp. As depicted in FIG. 2A, the two surfaces 252, 254 are angled with respect to a longitudinal axis of the first clamp component 230. The triangular protrusion formed by the two surfaces 252, 254 may be capable of latching into the attachment portion 306 of the cannula 300 when the attachment portion 306 is received in the region between the two clamp components 220, 230 and the first clamp component is in its closed position, as shown in FIGS. 5C and 6. The attachment portion 306 may have two surfaces 308, 310 (see FIG. 3) that form a shape or structure that is configured to mate with the triangular protrusion formed by the two surfaces 252, 254. In some variations, the locating structure may include additional angled or tapered surfaces and take on different shapes (e.g., a frusto-pyramidal shape, as further described below with reference to FIGS. 9A and 9B).

In some aspects, the two clamp components 220, 230 may be non-sterile and the cannula 300 may be sterile. Thus, a sterile barrier can be provided that separates the non-sterile clamp components 220, 230 from the sterile cannula 300. As depicted in FIG. 3, a sterile adapter 212 may form a sterile barrier between the non-sterile clamp components 220, 230 and the sterile cannula 300. The sterile adapter 212 can be a cover that has an opening 211 (see FIGS. 2C and 3) for receiving the attachment portion 306 of the cannula 300 such that, the attachment portion 306, when received in the sterile adapter 212, is covered or surrounded by the sterile adapter 212. The sterile adapter 212 may be sufficiently flexible such that it can deform (e.g., receive the attachment portion 306 when the attachment portion 306 is inserted through the opening 211) but have sufficient stiffness such that it retains a non-deformed or resting shape that generally corresponds to a shape of the attachment portion 306 of the cannula 300. In particular, in its non-deformed state, the sterile adapter 212 may form a shape with two tapered surfaces 202, 204 that substantially corresponds to the shape formed by the two tapered surfaces 308, 310 of the attachment portion 306.

The sterile adapter 212 may be mounted to and supported by a support component 210 such as, for example, a bar or beam. As shown in FIG. 3, the support component 210 may include one or more engagement mechanisms 216 that are configured to releasably couple or attach the support component 210 to the support component 214 (described above). For example, the engagement mechanism 216 may include a latch that latches onto an edge or ridge 218 of the support component 214. Additionally or alternatively, the engagement mechanism 216 may include a hook, a screw, a pin, and/or other mechanism capable of coupling the support component 210 to the support component 214. In some aspects, an adhesive may additionally or alternatively be used to couple the support component 210 to the support component 214. When the support component 210 is attached to the support component 214, the sterile adapter 212 may be disposed in the region between the two clamp components 220, 230, as depicted in FIGS. 2A-2C and 4A-6.

FIGS. 4A-5C show the attachment device 200 in different configurations during a cannula attachment or coupling operation. As depicted in FIG. 4A, the locking component 240 is positioned in the unlocked position and the first clamp component 230 is positioned in the open position. The cannula 300 may be moved in a direction 410 such that the attachment portion 306 of the cannula 300 is inserted into the region between the two clamp components 220, 230 or, more specifically, inserted through the opening 211 into the sterile adapter 212, which is located in the region between the two clamp components 220, 230. In some variations, the surface 254 of the first clamp component 230 may be configured to help guide and orient the attachment portion 306 when it is inserted into the region between the two clamp components 220, 230. For example, the surface 254 may be angled such that it smoothly receives the attachment portion 306 when the attachment portion 306 is inserted into the region between the two clamp components 220, 230 in the predefined orientation shown in FIG. 4A (e.g., in an orientation where the surfaces 308, 310 are facing the surfaces 252, 254 and configured to engage or mate with surfaces 252, 254, as shown in FIG. 5C). And when the attachment portion 306 is inserted into the region between the two clamp components 220, 230 in a different orientation, the surface 254 may push against or otherwise interfere with the attachment portion 306 to indicate that the attachment portion 306 is not properly orientated with respect to the two clamp components 220, 230. For example, the first surface 254 may prevent the attachment portion 306 from being inserted into the region between the two clamp components 220, 230 (e.g., by creating a clearance that is too small for the attachment portion 306 to be inserted into the region) when the attachment portion 306 is not being inserted into the region between the two clamp components 220, 230 in the predefined orientation. Additionally or alternatively, the first surface 254 may exert a backward force against the attachment portion 306 (via interference between the first surface 254 and the attachment portion 306) when the attachment portion 306 is not being inserted into the region in the predefined orientation, which may signal to a user that the attachment portion 306 is not properly orientated with respect to the two clamp components 220, 230. In some variations, to help guide the attachment portion 306 into the region between the two clamp components 220, 230, the first surface 254 may be angled to generally correspond to an angle of the surface 312 of the attachment portion 306 when the first clamp component 230 is in the open position. Accordingly, as the attachment portion 306 is being inserted into the region between the two clamp components 220, 230, the first surface 254 may contact the surface 312 and help guide the attachment portion 306 into the region between the two clamp components 220, 230.

In some variations, the second clamp component 220 may have an angled or tapered surface that can guide the attachment portion 306 into the region between the two clamp components 220, 230 in the predefined orientation. As depicted in FIG. 4A, the second clamp component 220 may have an angled surface 206 that is shaped to correspond to a bottom surface 314 of the attachment portion 306. The angled surface 206 may be slightly angled toward the first clamp component 230 such that it creates a slight taper in the region between the two clamp components 220, 230. Accordingly, when the attachment portion 306 is being inserted into the region between the two clamp components 220, 230, the second clamp component 220 may contact and help guide the attachment portion 306 into the region.

After the attachment portion 306 is inserted into the region between the two clamp components 220, 230, the locking component 240 may be moved from its unlocked position to its locked over-center position by pivoting the locking component 240 in a direction 420, as shown in FIG. 4B. FIGS. 5A-5C show the locking component 240 in different configurations as it is pivoted from its unlocked position to its locked over-center position. In the variation depicted, the first clamp component 230 may have a slot 232 formed along a longitudinal length of its body. The slot 232 may extend along a partial length of the first clamp component 230. The locking component 240 may have a first end 250 that is movable along a length of the slot 232. In particular, the locking component 240 may have a peg located at its first end 250 that is disposed in and movable along a length of the slot 232. The locking component 240 may have a second end 242 that is shaped like a handle or knob. The locking component 240 may have a shaft 248 that extends from the second end 242 of the locking component 240 through the second pivot point 244 to the first end 250 of the locking component 240. The second end 242 of the locking component 240 may be movable, for example, by a user, to pivot the locking component 240 between the unlocked position and the locked over-center position. For example, a user may apply a force 420, as shown in FIG. 4B, to move the second end 242 of the locking component 240 in order to pivot the locking component 240 from the unlocked position to the locked over-center position. The user may apply the force 420 by pressing on or pushing the second end 242 of the locking component 240.

In FIG. 5A, the first end 250 of the locking component 240 has moved a first distance in a first direction along a slot 232 of the first clamp component 230. As the locking component 240 continues to pivot, the first end 250 of the locking component 240 may continue to move along the slot 232 in the first direction to a dead-center position, as shown in FIG. 5B. In the dead-center position, the shaft 248 (including portions 248a, 248b) of the locking component 240 may be aligned along the axis 430. In the example shown in FIG. 5B, once the locking component 240 has pivoted to the dead-center position, the locking component 240 has moved the first clamp component 230 approximately to the closed position, and further movement of the locking component 240 beyond the dead-center position does not cause significant additional movement of the first clamp component 230. Although the first clamp component 230 is shown in FIG. 5B as being approximately in the closed position when the locking component 240 has pivoted to the dead-center position, in other variations, the first clamp component 230 may be in a position that is offset from the closed position. In some variations, the first clamp component 230 may be formed of a compressible material that begins and/or continues to deform as the locking component 240 pivots beyond the dead-center position. In some variations, the locking component 240 may be balanced in place when it is in the dead-center position. For example, if a user applies just enough force to move the locking component 240 into the dead-center position and does not exert additional force to move the locking component 240 beyond the dead-center position, then the locking component 240 can stay balanced in the dead-center position.

When additional force is exerted on the locking component 240 in the direction 420, the locking component 240 may pivot until it is in the locked over-center position, as shown in FIG. 5C. Once the locking component 240 is pivoted beyond the dead-center position (e.g., as shown in FIG. 5C), a biasing force may act on the locking component 240 and force it to continue pivoting until the locking component 240 is in the locked over-center position. The biasing force acting on the locking component 240 holds the locking component 240 in the locked over-center position until a sufficient counter-force overcomes the biasing force to move the locking component 240 back toward its initial unlocked position. Accordingly, a user must overcome the additional biasing force that acts on the locking component 240 before the user can move the locking component 240 back to its unlocked position and open the first clamp component 230. In the locked over-center position, the first end 250 of the locking component 240 may be disposed at a far end of the slot 232 (e.g., an end opposite from an end of the slot closer to the pivot point 234), and the first clamp component 230 may be in the closed position. Accordingly, by moving or pivoting the locking component 240 from the unlocked position to the locked over-center position, a user may pivot the first clamp component 230 into the closed position.

When the first clamp component 230 is in the closed position, the two clamp components 220, 230 may retain the attachment portion 306 of the cannula 300 in the region between the two clamp components 220, 230. In some variations, the locking component 240 acts to prevent the cannula 300 from becoming disengaged or decoupled from the attachment device 200. For example, as depicted in FIG. 6, when the locking component 240 is in the locked over-center position and the cannula 300 is retained between the two clamp components 220, 230, a pulling force applied in a direction 502 creates a force that pushes upward in a direction 504, which acts to pivot the locking component 240 in a direction 506, further pushing the locking component 240 toward the locked over-center position. The pulling force may result from a force being applied to a portion of the cannula 300 (e.g., the proximal portion 302 or the shaft 304), such as, for example, during a surgical operation or procedure. As described above, the first clamp component may have a surface 252 that is configured to mate and engage with a surface 310 of the attachment portion 306. Accordingly, when the cannula 300 is pulled in the direction 502, the surface 252 may engage with the surface 310, which creates a force in the direction 504. The force in the direction 504 then acts on the second portion 248b of the shaft 248 to pivot the locking component 240 in the direction 506.

Figure 16:
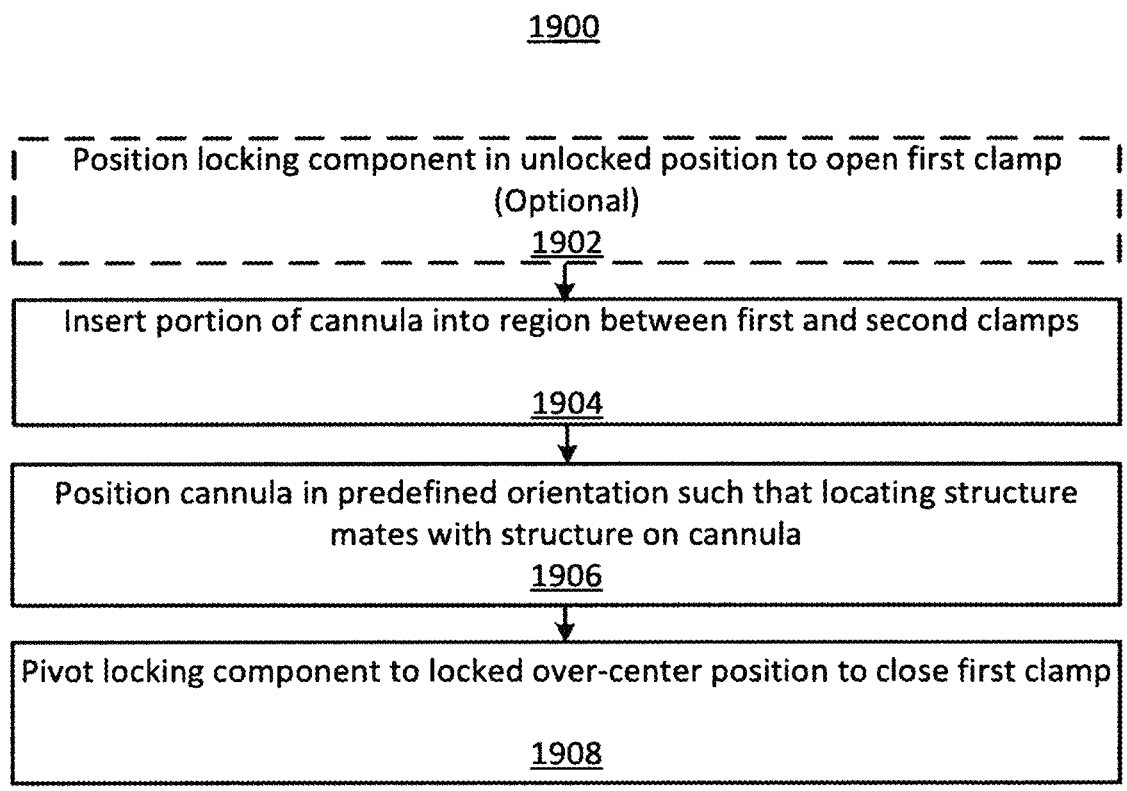
FIG. 16 is a flowchart of an exemplary method for attaching a cannula to a robotic surgical system using a cannula attachment device.

FIG. 16 is a flowchart of an exemplary variation of a method 1900 of attaching a cannula to a surgical system using an attachment device, such as the attachment device 200 or other attachment devices described herein. The method 1900 may optionally include positioning a locking component (e.g., the locking component 240) of the attachment apparatus in an unlocked position, at 1902. The locking component may be operatively coupled to a clamp component (e.g., the first clamp component 230) and configured to pivot the clamp component between an open position and a closed position. The locking component may pivot the clamp component to the open position when the locking component is positioned in the unlocked position. In the open position, the clamp component may allow a portion of a cannula (e.g., the attachment portion 306 of the cannula 300) to be received in a region between the clamp component and another clamp component (e.g., the second clamp component 220). Accordingly, when the locking component is not in the unlocked position and the clamp component is not in the open position, the locking component may be moved into the unlocked position in order to position the clamp component in the open position, at 1902. When the locking component is already in the unlocked position and the clamp component is in the open position, step 1902 may be omitted.

At 1904, the portion of the cannula (e.g., the attachment portion 306 of the cannula 300 may be inserted into the region between the two clamp components (e.g., the two clamp components 220, 230). The cannula may be positioned in a predefined orientation relative to the two clamp components, at 1906. When the cannula is in the predefined orientation relative to the two clamp components, a locating structure disposed on at least one of the two clamp components (e.g., the locating structure defined by the two surfaces 252, 254) may mate with a corresponding structure disposed on the portion of the cannula (e.g., the surfaces 308, 310) after the cannula is fully inserted into the region between the two clamp components. At 1908, the locking component may be moved from the unlocked position to a locked over-center position in order to pivot the clamp component to the closed position. When the clamp component is in the closed position, the two clamp components may retain the portion of the cannula in the region between the two clamp components. For example, the two clamp components may clamp around the portion of the cannula such that the portion of the cannula is held or secured in the region between the two clamp components. The locating structure or some other structure disposed on one of the two clamp components or another surface adjacent to the region between the two clamp components may latch into a corresponding structure disposed on the portion of the cannula to retain the portion of the cannula in the region between the two clamp components.

Figure 7A:
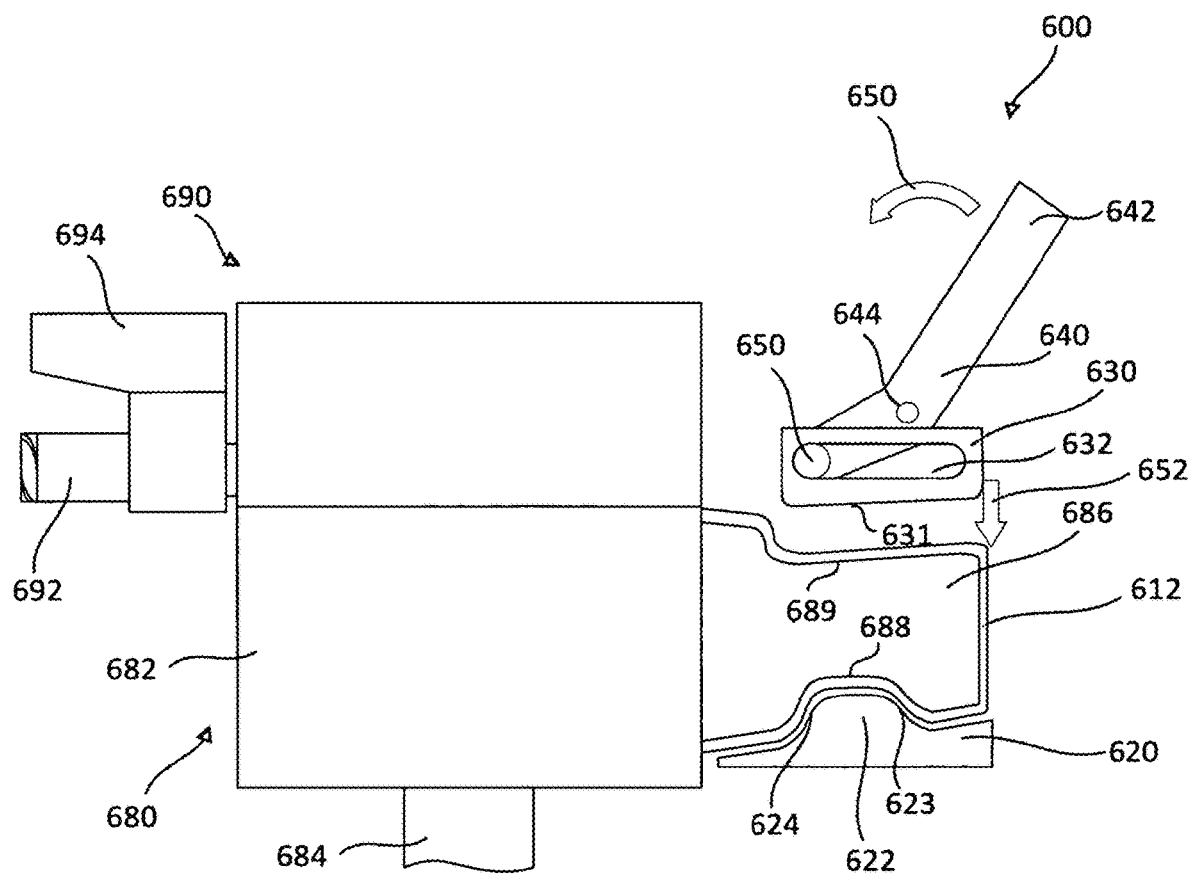
FIGS. 7A and 7B are schematic illustrations of another exemplary variation of a cannula attachment device.
Figure 7B:
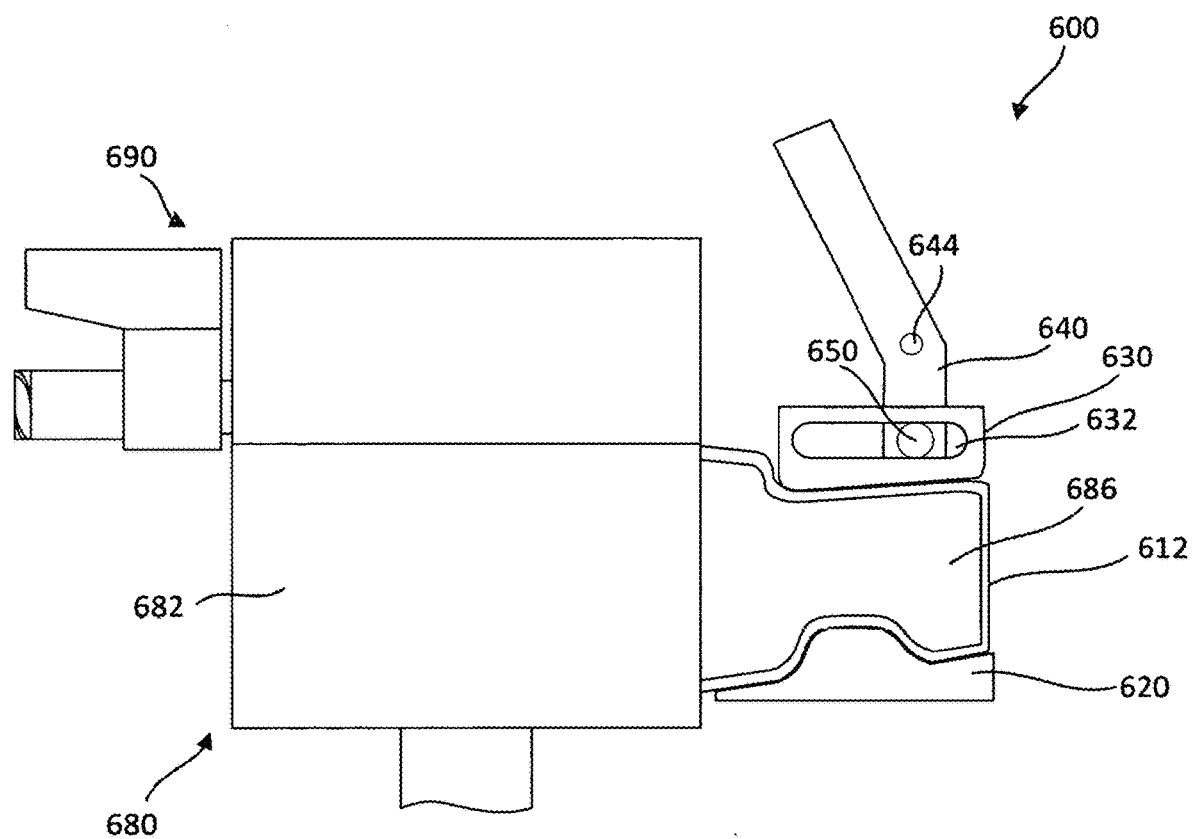

FIGS. 7A and 7B depict another exemplary variation of an attachment device for mounting a cannula, such as a cannula 680, having two clamp components. FIGS. 7A and 7B show the attachment device 600 in two different configurations—specifically, FIG. 7A depicts the attachment device 600 in a first configuration in which a clamp component 630 of the attachment device 600 is in an open position, and FIG. 7B depicts the attachment device 600 in a second configuration in which the clamp component 630 is in a closed position. The attachment device 600 may be similar in structure and/or function to one or more other attachment devices described herein, including the attachment device 200 described with reference to FIGS. 2A-6, with variations including, for example, (1) a locating structure being located on a fixed clamp component instead of a movable clamp component, and (2) the movable clamp component 630 is moveable or translatable in a direction 652 instead of pivotable. As shown in FIG. 7A, the attachment device 600 may include the clamp component 630 and an additional clamp component 620. The two clamp components 620, 630 may define a region between them in which an attachment portion 686 of the cannula 680 may be received.

The cannula 680 may be similar in structure and/or function to one or more other cannula variations described herein, including the cannula 300 described with reference to FIGS. 3-6. For example, the cannula 680 may include a proximal portion 682 and a shaft 684. The shaft 684 may have a lumen through which a surgical instrument 690 may be inserted. The surgical instrument 690 may include a port 692 through which a fluid may be introduced into and/or removed from the body of the patient. The flow of fluid in and/or out of the port 692 may be controlled by a valve control 694. The proximal portion 682 of the cannula 680 may include the attachment portion 686.

The attachment device 600 may also include a locking component 640 (e.g., a lever, bar, beam, or similar structure), which is configured to pivot about a pivot point 644. The locking component 640 may be operatively coupled to the clamp component 630 via a peg 650 (or other structure) that fits into a slot 632 formed in the clamp component 630. The peg 650 may be configured to move along a length of the slot 632. Similar to the attachment device 200, the locking component 640 may be configured to move the clamp component 630 between the open position and the closed position. When the locking component is in a first unlocked position, the clamp component 630 may be in the open position (as depicted in FIG. 7A), and when the locking component is in a second locked, over-center position, the clamp component 630 may be in the closed position (as depicted in FIG. 7B). The locking component 640 may include a handle 642 disposed at an end opposite from the end coupled to the clamp component 630. When the locking component 640 pivots to its locked over-center position, the clamp component 630 may move in a direction 652, as shown in FIG. 7A, to its locked position.

When the locking component 640 is in the locked over-center position, the attachment portion 686 of the cannula 680 may be retained in the region between the two clamp components 620, 630, as shown in FIG. 7B. Similar to the attachment device 200, the over-center locking arrangement of the locking component 640 reduces a risk that the locking component 640 may inadvertently pivot from its locked over-center position to its unlocked position. When the locking component 640 is in the locked over-center position, the locking component 640 may be biased toward the locked over-center position such that a biasing force must be overcome before the locking component 640 can be pivoted back to its unlocked position. This biasing force results from the over-center arrangement of the locking component 640, similar to the over-center arrangement of the locking component 240 of the attachment device 200, described above. The locking component 640 and the two clamp components 620, 630 may be supported on a support (not depicted). The locking component 640 may be movably supported on the support via the pivot point 644; the clamp component 620 may be fixedly supported on the support; and the clamp component 630 may be movably supported on the support via a second pivot point or a track (not depicted) that allows the clamp component 630 to move relative to the support.

The attachment device 600 may have a locating structure that is configured to mate with a corresponding structure disposed on the attachment portion 686 of the cannula 680. In the variation shown in FIGS. 7A and 7B, the locating structure may be a protrusion 622 disposed on the fixed clamp component 620. In other variations, such as the variation depicted in FIGS. 2A-6, the locating structure can be disposed on a moveable clamp component. Additionally or alternatively, one or more locating structures can be disposed on one or both clamp components 620, 630, or another component or surface adjacent to the region between the two clamp components 620, 630. The protrusion 622 may have a plurality of tapered or angled surfaces. The protrusion 622 may be configured to fit into and mate with a recess 688 formed in the attachment portion 686 of the cannula 680. When the clamp component 630 is in the closed position (as shown in FIG. 7B) and the protrusion 622 has mated with the recess 688, the protrusion 622 can prevent the cannula 680 from being removed or detached from the attachment device 600. For example, the protrusion 622 may have an angled surface 623 with a deep pull-back angle that prevents the attachment portion 686 of the cannula 680 from being pulled out of the region between the two clamp components 620, 630. The clamp component 630 may have a surface 631 that is slightly angled, for example, by an angle of five degrees relative to a longitudinal axis of the clamp component 630. When the clamp component 630 is in the closed position, the angled surface 631 may clamp down on a surface 689 of the attachment portion 686, which may be angled to correspond to the angle of the surface 631. The angled surface 631 and the correspondingly angled surface 689 may further help to retain the attachment portion 686 in the region between the two clamp components 620, 630.

Similar to the locating structure of the cannula attachment device 200, the protrusion 622 may be capable of guiding the attachment portion 686 into the region between the two clamp components 620, 630 in a predefined orientation relative to the two clamp components 620, 630. For example, the protrusion 622 can have an angled surface 624 that helps a user determine whether the attachment portion 686 is being received in the region between the two clamp components 620, 630 in a predefined orientation relative to the two clamp components 620, 630. The angled surface 624 may indicate to the user where the locating structure (e.g., protrusion 622) is disposed such that the user can orient the cannula 680 to align the recess 688 of the attachment portion 686 with the protrusion 622 when inserting the attachment portion 686 into the region between the two clamp components 620, 630.

In some variations, the two clamp components 620, 630 may be non-sterile and the cannula 680 may be sterile. Thus, the attachment device 600 may provide a sterile barrier that separates the non-sterile clamp components 620, 630 from the sterile cannula 680. As depicted in FIGS. 7A and 7B, a sterile adapter 612 may form a sterile barrier between the non-sterile clamp components 620, 630 and the sterile cannula 680. Similar to the sterile adapter 212 of the cannula attachment device 200, the sterile adapter 612 may be a cover with an opening for receiving the attachment portion 686 of the cannula 680.

Figure 8:
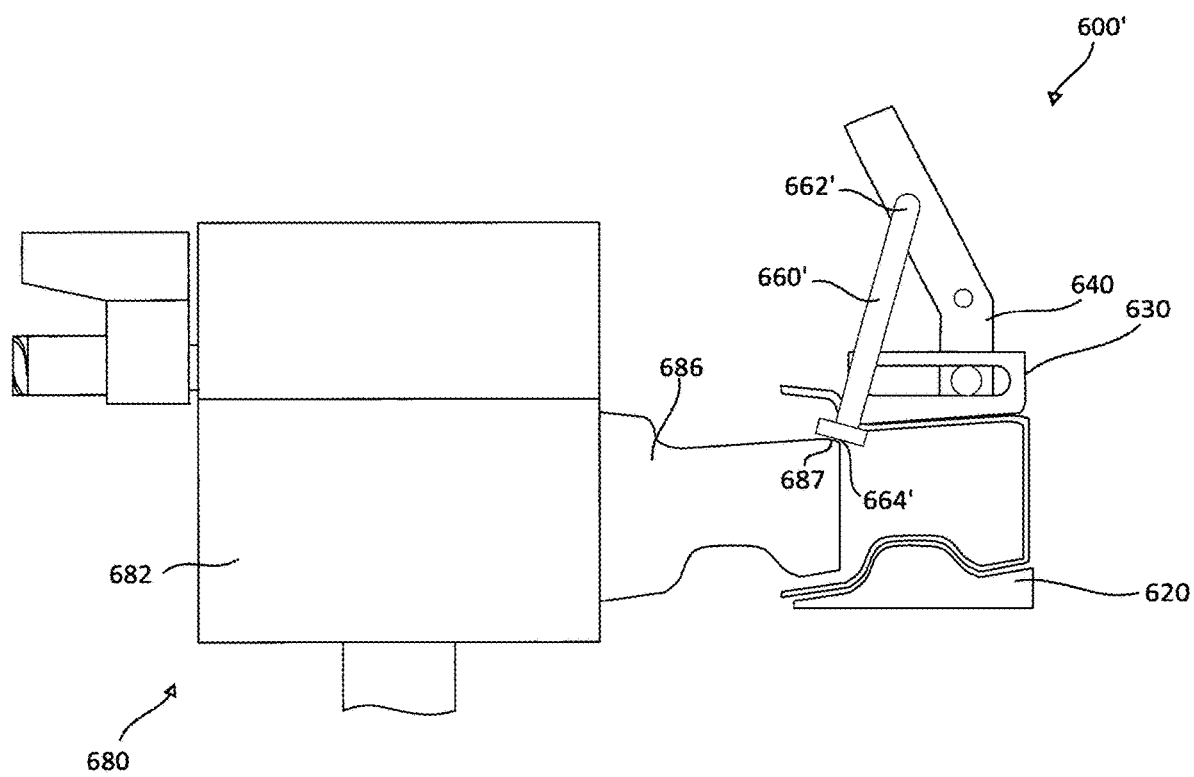
FIG. 8 is a schematic illustration of another exemplary variation of a cannula attachment device, including a mechanism for moving a locking component.

In some variations, the attachment device 600 may have a biasing element such as a spring that biases the locking component 640 to its locked over-center position, thereby holding the clamp component 630 in the closed position. In these variations, the locking component 640 must first be moved from its locked over-center position to its unlocked position in order to allow the attachment portion 686 of the cannula 680 to be inserted into the region between the two clamp components 620, 630. A user may move the locking component 640 to its unlocked position by overcoming the biasing force of the spring. Once the attachment portion 686 is inserted into the region between the two clamp components 620, 630, the user may release the locking component 640, thereby allowing the spring to bias the locking component 640 back to its locked over-center position to close the clamp component 630 down on the attachment portion 686. Alternatively, an additional intermediate mechanism, such as a lever or plate, may be capable of moving the locking component 640 to its unlocked position as the attachment portion 686 is being inserted into the region between the two clamp components 620, 630, thereby enabling the attachment portion 686 to transition the clamp component 630 from a closed position to an open position. For example, as depicted in FIG. 8, an alternative attachment device 600' may have an intermediate mechanism 660' that can move a locking component 640. The attachment device 600' may have similar components as the attachment device 600, with like numerals referring to like parts, but also have the mechanism 660'. The attachment device 600' may have a spring (not depicted) that biases the locking component 640 to its locked over-center position. The intermediate mechanism 660' may have a surface 664' that is first contacted by a leading surface 687 of the attachment portion 686 when the attachment portion 686 is being advanced into the region between the two clamp components 620, 630. As the attachment portion 686 is advanced further into the region between the two clamp components 620, 630, the leading surface 687 of the attachment portion 686 may continue to press against the surface 664' of the intermediate mechanism 660', which may cause another portion of the intermediate mechanism 660' (e.g., a portion 662' disposed at an opposite end of the mechanism 660') to apply a force against the locking component 640. Once a force sufficient to overcome the biasing force of the spring is applied against the locking component 640, the locking component 640 may move from its locked over-center position to its unlocked position. In the unlocked position, the locking component 640 may release the clamp component 630 (e.g., allow the clamp component 630 to open), thereby allowing the attachment portion 686 to be advanced further into the region between the two clamp components 620, 630. Then, once the attachment portion 686 has advanced a certain distance into the region between the two clamp components 620, 630, the mechanism 660' may disengage with the attachment portion 686 and move aside, thereby allowing the spring to bias the locking component 640 to its locked over-center position once again and to close the clamp component 630 down on the attachment portion 686.

Figure 9A:
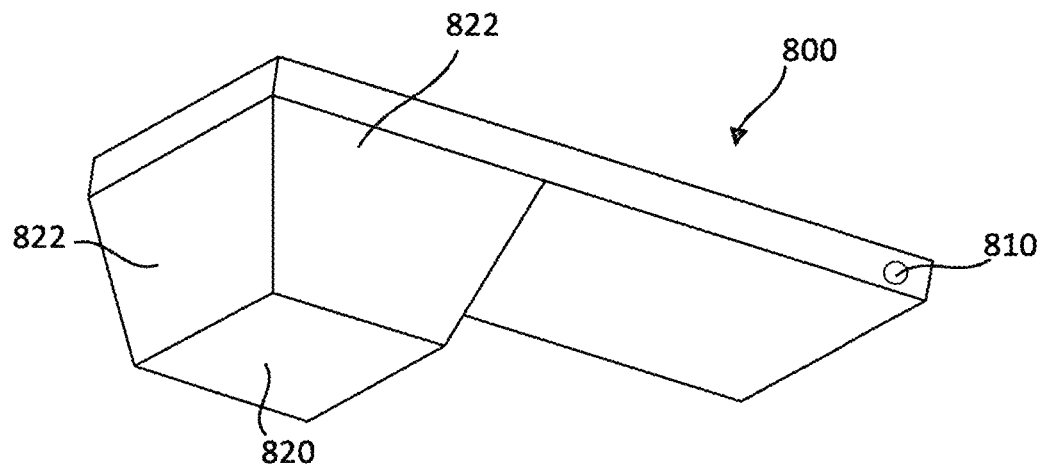
FIG. 9A is a schematic illustration of an exemplary variation of clamping component of a cannula attachment device having a locating structure.
Figure 9B:
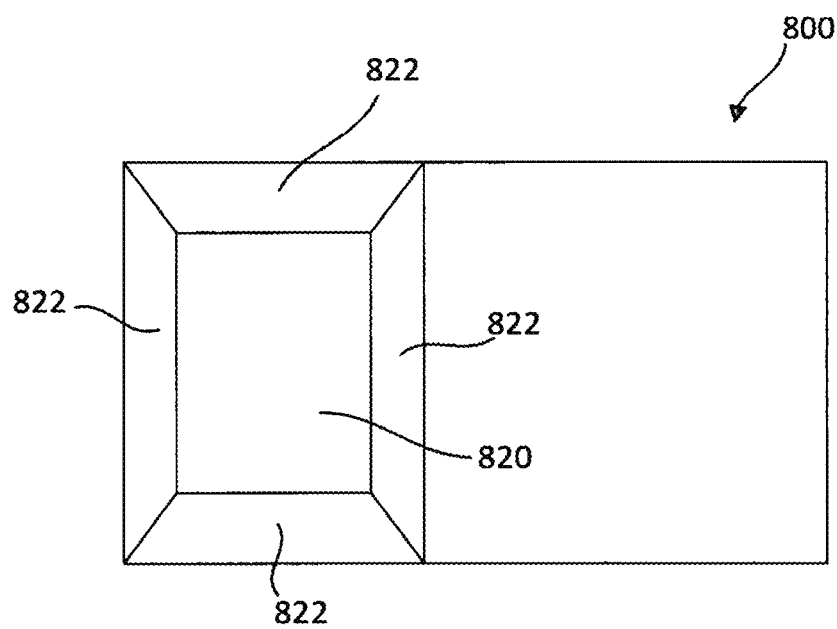
FIG. 9B is a side view of the clamping component depicted in FIG. 9A.

In some variations, a cannula attachment device may have a locating structure having a frusto-pyramidal shape, such as, for example, a four-sided sloped pyramid shape or other tapered pyramidal shape. The locating structure can be located on a movable clamp component, a fixed clamp component, or another component or surface surrounding a region that receiving a portion of a cannula. For example, as shown in FIGS. 9A and 9B, a moveable clamp component 800 may have a locating structure formed of a flat surface 820 and four angled surfaces 822. The multiple surfaces 820, 822 of the locating and attaching structure may allow a cannula or trocar to be securely positioned and attached to a robotic arm of a surgical robotic system. For example, the moveable clamp component 800 may be coupled to a surgical robotic system (e.g., a tool driver or an end of a robotic arm), and the locating and attaching structure of the moveable clamp component 800 may be configured to mate with a corresponding structure disposed on a portion of the cannula or trocar. When the locating and attaching structure mates with the corresponding structure of the cannula or trocar, the locating and attaching structure may secure the cannula or trocar in place relative to the robotic arm. The movable clamp component 800 may be held or clamped in place over a portion of the cannula or trocar by a locking assembly such as any of the locking components described herein. The movable clamp component 800 may have an opening 810 (or, alternatively, a peg) for engaging with additional structure to form a pivot point about which the movable clamp component 800 may pivot. When set up, the movable clamp component 800 may pivot between an open position and a closed position, similar to that of clamp component 230 and clamp component 630. In some variations, the movable clamp component 800 may have a slot that allows a locking component, such as any of the locking components described herein, to moveably couple to the movable clamp component 800 via a peg or similar structure.

Figure 10:
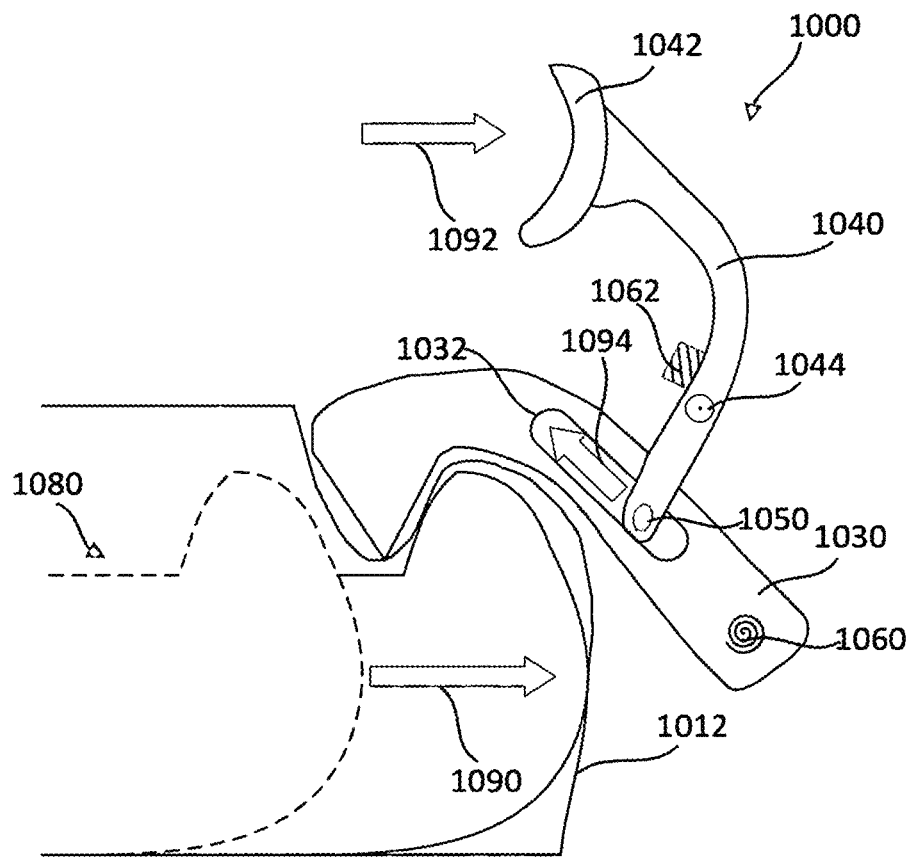
FIG. 10 is a schematic illustration of another exemplary variation of a cannula attachment device.

FIG. 10 depicts another exemplary variation of an attachment device for mounting a cannula, such as a cannula 1080, having a two-member lock and release system. The attachment device 1000 can be similar in structure and/or function to one or more other attachment devices described herein, including the attachment device 200 described with reference to FIGS. 2A-6, with variations including, for example, (1) a spring 1060 configured to bias a clamp component 1030 to a closed position, and (2) one or more stop surfaces 1062 configured to limit a movement of a locking component such as, for example, a release lever 1040. The attachment device 1000 may have a clamp component 1030, such as a lever or bar, which can move between an open position and a closed position. The clamp component 1030 may be biased to the closed position, as shown in FIG. 10, by a spring 1060, such as a torsion spring. The attachment device 1000 may have a release lever or bar 1040, which can move the clamp component 1030 from the closed position to the open position. The release lever 1040 may have a first end that is moveably coupled to the clamp component 1030 via a peg 1050. The peg 1050 may be disposed in a slot 1032 formed in the clamp component 1030 and configured to slide along a length of the slot 1032. The release lever 1040 may also have a second end with a user contact point or handle 1042 that can be actuated, e.g., by a hand of a user, to move the release lever 1040. The movement of the release lever 1040 may be limited by one or more stop surfaces 1062. The handle 1040 can be pushed or pressed by a user in a direction 1092 to move the first end of the release lever 1040 in a direction 1094 (e.g., to translate the peg 1050 along the length of the slot 1032 in the direction 1094). When the first end of the release lever 1040 moves in the direction 1032, the release lever 1040 may exert a force on the clamp component 1030 that can overcome the biasing force of the spring 1060 and move the clamp component 1030 from the closed position to the open position. In the open position, the clamp component 1030 may allow a portion of the cannula 1080 to be inserted in a direction 1090 into a region of the attachment device 1000. When the user stops pressing on the handle 1040, the spring 1060 may bias the clamp component 1030 back to its closed position, and the clamp component 1030 may latch onto the portion of the cannula 1080 to retain that portion in the region of the attachment device 1000.

Similar to the locking components described herein, the release lever 1040 may be designed as an over-center locking mechanism. For example, when the release lever 1040 is in the position shown in FIG. 10, the release lever 1040 may be in an over-center position. In the over-center position, the release lever 1040 may biased to remain in the over-center position (e.g., biased against moving). Due to its over-center arrangement, the release lever 1040 may experience a biasing force that holds the release lever 1040 in its locked over-center position.

In some variations, the attachment device 1000 may have an additional clamp component or a fixed surface spaced from the clamp component 1030. The clamp component 1030 and this additional clamp component may define the region for receiving the portion of the cannula 1080. When the portion of the cannula 1080 is disposed in the region defined by the clamp component 1030 and the additional clamp component, and the user releases the release lever 1040 such that the clamp component 1030 moves back to its closed position, the clamp component 1030 and the additional clamp component may clamp around the portion of the cannula 1080 to retain it within the region defined by the clamp component 1030 and the additional clamp component.

Similar to other cannula attachment devices described herein, the attachment device 1000 may also have a sterile adapter 1012 for providing a sterile barrier between the clamp component 1030, which may be non-sterile, and the cannula 1080, which may be sterile.

Ratchet-Like Variations

In some variations, a cannula attachment device may have a mechanism for attaching a cannula to a tool driver or robotic arm that allows the cannula to be easily inserted into a region of the attachment device in one direction but difficult to remove in another direction. In such variations, a user may not need to actuate a component of the attachment device in order to insert and securely attach the cannula to the attachment device. The attachment device may be designed to allow the cannula to be attached to the attachment device when the cannula is brought into contact with a portion of the attachment device.

Figure 11:
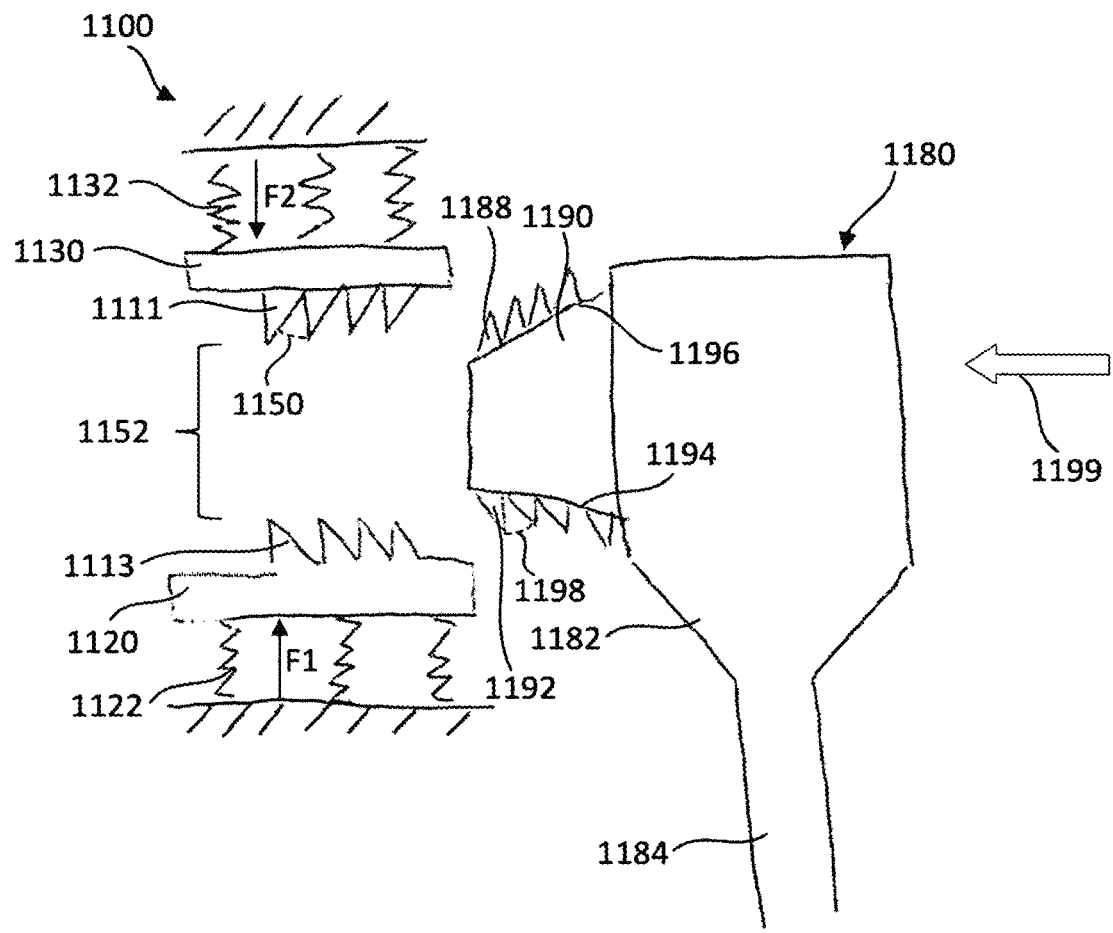
FIG. 11 is a schematic illustration of another exemplary variation of a cannula attachment device.

For example, an exemplary variation of a cannula attachment device 1100 is depicted in FIG. 11. The cannula attachment device 1100 is configured to receive a cannula 1180 having a cannula proximal portion 1182 and a cannula shaft 1184 extending distally from the cannula proximal portion 1182.

The cannula proximal portion 1182 may have a projection 1190 (e.g., an attachment portion) extending from a side of the cannula proximal portion 1182, where the projection 1190 generally tapers in width. For example, the projection 1190 may generally have a shape of a trapezoidal prism with two opposite sides of the projection 1190 tapering toward a centerline of the projection, or a shape of a square frustum with four sides of the projection 1190 tapering toward centerline of the projection. The projection 1190 may include angled teeth 1188 arranged on a first tapering side 1196 and angled teeth 1192 arranged on a second tapering side 1194. The angled teeth 1188, 1192 may be angled away from a direction generally perpendicular to an insertion direction (e.g., the insertion direction 1199) at an angle 1198. The angle 1198 may be, for example, between about 15 and about 50 degrees, or between about 20 and about 45 degrees, or between about 30 and about 35 degrees. The angled teeth 1188 may be angled in a direction opposite from that of the angled teeth 1192.

The cannula attachment device 1100 may include at least two plates 1120, 1130 that are opposing each other across an opening or region 1152 for receiving the cannula projection 1190. The plate 1120 may have angled teeth 1113 disposed on a surface facing the opening 1152, and the plate 1130 may have angled teeth 1111 also disposed on a surface facing the opening 1152. The angled teeth 1111, 1113 may be angled relative to a direction generally perpendicular to the insertion direction 1199 by an angle 1150. The angle 1150 may be, for example, between about 15 and about 50 degrees, or between about 20 and about 45 degrees, or between about 30 and about 35 degrees. The angle 1150 may correspond to the angle 1198 such that the angled teeth 1188, 1192 can matingly engage with the angled teeth 1111, 1113. Similar to the angled teeth 1188, 1192, the angled teeth 1111 may be angled in a direction opposite from that of the angled teeth 1113. The plate 1120 may be urged toward the plate 1130 by a biasing element such as a spring 1122 applying a bias force F1, and the plate 1130 may be urged toward the plate 1120 by another biasing element such as a spring 1132 applying a bias force F2.

To attach the cannula 1180 to the attachment device 1100, the cannula 1180 may be moved toward the attachment device 1100 in an insertion direction 1199 to insert the cannula projection 1190 into the opening 1152. Insertion of the cannula projection 1190 into the opening 1152 may displace the adapter plates 1120, 1130 apart to enable the angled teeth 1188 to engage with the angled teeth 1111 and the angled teeth 1192 to engage with the angled teeth 1113. Once the angled teeth 1188, 1192 are engaged with the angled teeth 1111, 1113, the bias forces F1, F2 on the plates 1120, 1130 cause the plates 1120, 1130 to clamp down on the projection 1190 and secure or lock the coupling of the cannula attachment device 1100 and the cannula 1180. In some variations, a mechanical stop and/or latch (e.g., to lock the plates 1120, 1130 in a clamping arrangement) may be included to help secure the coupling. Generally, as long as at least one of the spring bias forces F1, F2 is not overcome, the relative movement of the cannula projection 1190 and the attachment device 1100 is permitted only in one direction, such that the cannula projection 1190 is easily inserted into the opening 1152 but is substantially prevented from being removed from the opening 1152. The springs 1122, 1132, may urge the plates 1120, 1130, respectively, toward one another to retain the projection 1190 within the opening 1152 as well as to maintain the engagement of the angled teeth 1111, 1113 with the angled teeth 1188, 1192, respectively. In some variations, a mechanism (e.g., a button, lever, handle, squeeze mechanism) may be provided to compress the springs 1122, 1132 by overcoming the spring bias force and to displace the plates 1120, 1130 sufficiently apart to permit removal of the cannula projection 1190 from the opening 1152, thereby decoupling the cannula 1180 from the attachment device 1100 (and a tool driver or robotic arm). Advantageously, in the exemplary variation shown in FIG. 11, the attachment device 1100 and the cannula 1180 may be coupled without requiring actuation of a secondary mechanism (e.g., the attachment device 1100 and the cannula 1180 may be coupled via a one-handed operation to "snap and lock" the cannula 1180 into the attachment device 1100), and the cannula 1180 may be securely retained with the attachment device 1100 until a secondary mechanism is activated to permit disengagement of the attachment device 1100 and cannula 1180.

Other variations of cannula attachment devices may also utilize angled teeth or similar angled features in different manners, such as for accommodating differently shaped cannula projections. For example, while the variation shown in FIG. 11 may be configured to receive a projection 1190 generally having the shape of a trapezoidal prism (with two opposite sides of the projection tapering toward the centerline of the projection) or a square frustum (with four sides of the projection tapering toward the centerline of the projection), other variations may be configured to receive other tapered projection shapes, such as a frusto-conical shape with annular angled ridges engaging angled teeth or ridges in the cannula adapter, or non-tapered projection shapes, such as a rectangular prismatic shape or cylindrical shape with angled teeth or ridges.

In some variations, a sterile adapter element for separating the non-sterile cannula attachment device 1100 from the sterile cannula 1180 may include a drape or other sterile sheet (e.g., plastic) that fits between the non-sterile angled teeth 1111, 1113 on the cannula attachment device 1100 and the sterile angled teeth 1188, 1192 on the cannula 1180. The plastic may act as a bearing surface with reduced friction between the teeth 1111, 1113, 1188, 1192, thereby further facilitating the insertion of the cannula projection 1190 into the cannula attachment device 1100.

Figure 12:
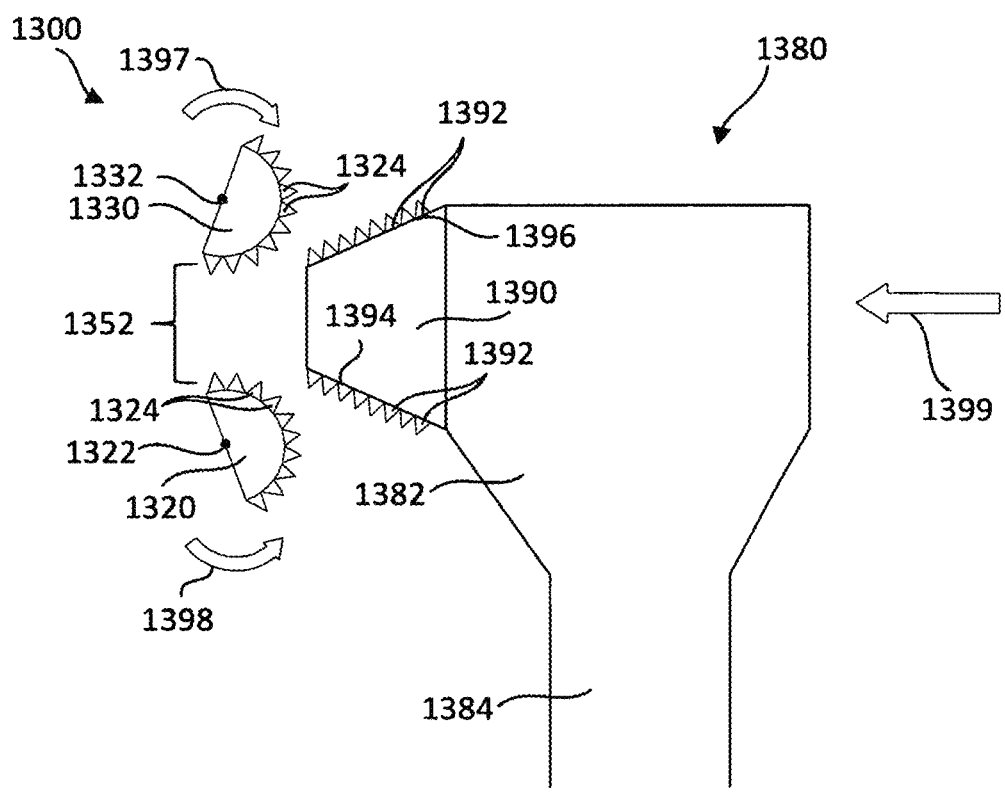
FIG. 12 is a schematic illustration of another exemplary variation of a cannula attachment device.

In another example variation, as shown in FIG. 12, a cannula attachment device 1300 is configured to receive a cannula 1380 having a cannula proximal portion 1382 and a cannula shaft 1384 extending distally from the cannula proximal portion 1382. Similar to the cannula 1180 shown in FIG. 11 and described above, the cannula proximal portion 1382 may have a projection 1390 (e.g., an attachment portion) extending from a side of the cannula proximal portion 1382, where the projection 1390 generally tapers in width (e.g., generally has the shape of a trapezoidal prism with two opposite sides of the projection 1390 tapering toward a centerline of the projection 1390). The projection 1390 may include teeth 1392 or similar structures arranged in a rack-like configuration on at least two tapering sides 1394, 1396 of the projection 1390. The cannula attachment device 1300 may include at least two rotating, pinion-like elements 1320, 1330 that are opposing each other across a space 1352 that receives the cannula projection 1390. Each of the pinon-like elements 1320, 1330 may include at least a portion of a gear, where a first side of the pinion-like element 1320, 1330 may be flat and a second side of that pinon-like element 1320, 1330 may be round and have teeth 1324 disposed thereon. The teeth 1324 of the pinion-like elements 1320, 1330 may be configured to engage the teeth 1392 on the cannula 1380. The pinon-like element 1320 may be configured to rotate about a point 1322, and the pinion-like element 1330 may be configured to rotate about a point 1332.

When the cannula projection 1390 is moved in a direction 1399 and inserted into the space 1352 between the two pinion-like elements 1320, 1330, the pinion-like element 1320 may rotate in a direction 1398 and the pinion-like element 1330 may rotate in a direction 1397, and the teeth 1392 on the cannula projection 1390 may engage with the teeth 1324 on the pinion-like elements 1320, 1330. Once the cannula projection 1390 has been inserted into the space 1352 between the two pinion-like elements 1320, 1330 and the teeth 1392 have engaged with the teeth 1324, the pinion-like elements 1320, 1330 may be locked into place by interfering elements acting on the flat surfaces of the pinion-like elements 1320, 1330. For example, the interfering elements may include springs that urge the pinion-like elements 1320, 1330 toward one another to clamp down on the projection 1390 and secure the coupling of the attachment device 1300 and the cannula 1380. The cannula projection 1390 may be easily inserted into the space 1352, but is substantially prevented from being removed from the space 1352 as a result of the springs urging the pinion-like elements 1320, 1330 toward one another to retain the projection 1390 in the space 1352. The interfering elements may include additional mechanical stops to help secure or lock the coupling. A mechanism (e.g., button, lever, handle, squeeze mechanism, etc.) may be included to overcome the force applied by the interfering elements in order to rotate the pinion-like elements 1320, 1330 in an opposite direction to permit removal of the cannula projection 1390 from the space 1352, thereby decoupling the cannula 1380 from a tool driver or robotic arm. Again, advantageously, in this variation, the cannula attachment device 1300 and the cannula 1380 may be coupled without requiring actuation of a secondary mechanism (e.g., the attachment device 1300 and the cannula 1380 may be coupled via a one-handed operation to "snap and lock" the cannula 1380 into the attachment device 1300), and the cannula 1380 may be securely retained with the attachment device 1300 until a secondary mechanism is activated to permit disengagement of the attachment device 1300 and cannula 1380.

Similar to the cannula attachment device 1100, other variations of the cannula attachment device 1300 may accommodate different shapes of the cannula projection 1390 (e.g., trapezoidal prism, square frustum, frusto-conical, etc.). And while the pinion-like elements 1320, 1330 are shown in FIG. 12 as being generally semi-circular, in other variations, the pinion-like elements 1320, 1330 may be circular (e.g., disk or ring-like with spokes, etc.) or include any suitable circular or round segment. Furthermore, in other variations, the pinion-like elements 1320, 1330 may have a varying radius such that, as the pinion-like elements 1320, 1330 rotate to receive the cannula projection 1390, the radius of the pinion-like elements 1320, 1330 where the teeth 1324 engage with the teeth 1392 may become increasingly narrower, thereby further securing the engagement between the pinion-like elements 1320, 1330 and the cannula projection 1390.

In some variations, a sterile adapter element for separating the non-sterile cannula attachment device 1300 from the sterile cannula 1380 may include an idler gear disposed between each non-sterile pinion-like element 1320, 1330 and the sterile projection 1390, which may provide physical separation between the non-sterile and sterile portions, while still permitting operation of a mechanism substantially similar to that described above with reference to FIG. 12. Additionally or alternatively, a drape or other sterile sheet may be disposed between the non-sterile teeth 1324 and sterile teeth 1392.

Figure 13:
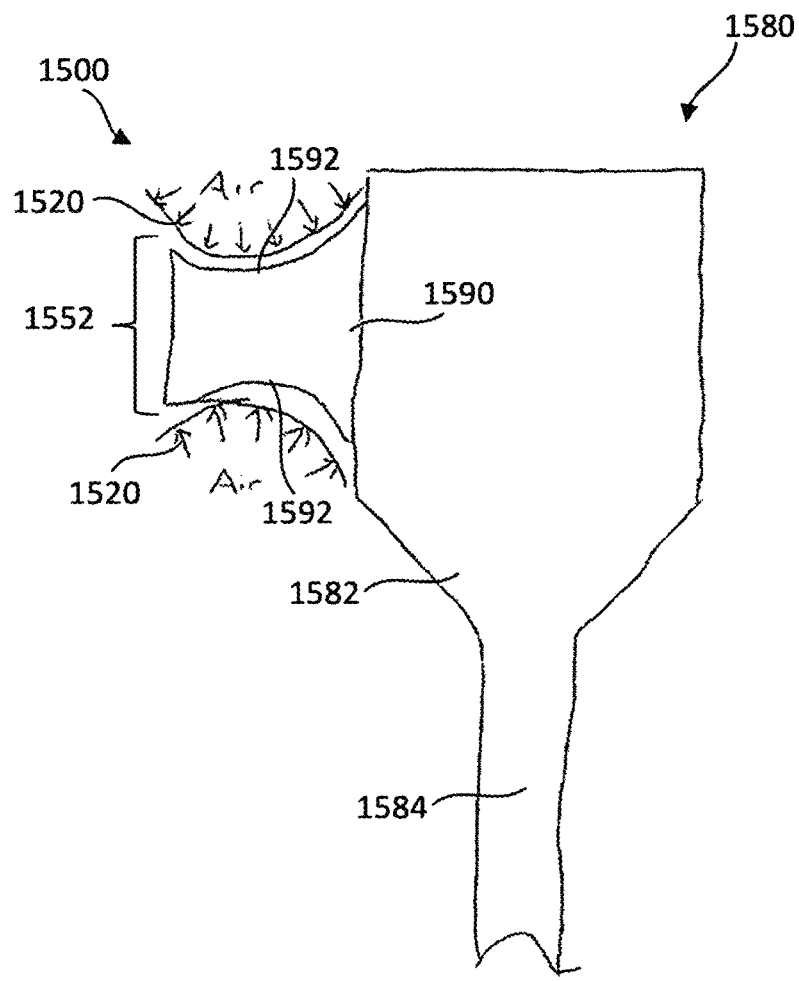
FIG. 13 is a schematic illustration of another exemplary variation of a cannula attachment device.

In another example variation, as shown in FIG. 13, a cannula attachment device 1500 is configured to receive a cannula 1580, where the cannula 1580 has a cannula proximal portion 1582 and a cannula shaft 1584 extending distally from the cannula proximal portion 1582. The cannula proximal portion 1582 may have a projection 1590 extending from a side of the cannula proximal portion 1582, where the projection 1590 has a contoured surface defining at least one concavity 1592. The concavity 1592 is configured to engage with at least one feature on the cannula attachment device 1500. For example, the cannula attachment device 1500 may include at least one inflatable bladder 1520, which may be selectively filled with a fluid (e.g., air or other gas, a liquid, etc.), such as through a valve and/or pump system. In one example, the projection 1590 may include a concavity 1592 such as an annular channel that extends around a perimeter of the projection 1590, and the bladder 1520 may be a torus-like structure configured to mate and engage with the annular channel. In another example, the projection 1590 includes at least one side with a concavity 1592 configured to engage with a single bladder 1520 of the cannula attachment device 1500. In yet another example, the projection 1590 includes at least two opposing sides with respective concavities 1592, each of which is configured to engage one of two bladders 1520 that oppose each other across a space or opening 1552 on the cannula attachment device 1500.

In a disengaged mode, the bladder 1520 may be deflated to permit the projection 1590 of the cannula 1580 to be inserted into the opening 1552. Once the projection 1590 is inserted into the opening 1552, the bladder 1520 may be inflated. In some variations, when the projection 1590 is inserted a predetermined distance or depth into the opening 1520, the projection 1590 may automatically trigger a valve to open and inflate the bladder 1520. The triggering mechanism may be a mechanical trigger or an electrical trigger, such as a contact sensor, pressure sensor, optical sensor, etc. Additionally or alternatively, a user may manually initiate inflation of the bladder 1520. In variations in which there are multiple bladders 1520 arranged in the cannula attachment device 1500, the multiple bladders may be symmetrically arranged and generally inflated to identical extents in order to automatically center and/or otherwise align the projection 1590 in the opening 1552, which may help to position and align other portions of the cannula 1580. Additionally or alternatively, at least some of the multiple bladders 1520 may be inflated to differing extents in order to compensate for misalignment of the projection 1590 and/or other portion of the cannula. Similarly, in variations in which there is a single bladder 1520, the bladder 1520 may be inflated to a selected extent in order to align the cannula and/or compensate for inherent misalignments in the cannula 1580. To disengage or remove the projection 1590 of the cannula 1580 from the attachment device 1500, the bladder 1520 may be deflated such that it is no longer engaged with the concavity 1592 in the projection 1590. A mechanism, such as a button or switch, may be actuated to release a valve or other component of a pump system to allow the bladder 1520 to deflate.

In some variations, a sterile adapter element for separating the non-sterile cannula attachment device 1500 from the sterile cannula 1580 may also include a drape or other sterile sheet (e.g., plastic) that fits between the non-sterile bladder 1520 on the cannula attachment device 1500 and the projection 1590 of the cannula 1580.

Cam Lock Variation

In some variations, a device for attaching a cannula to a tool driver may include a cam lock mechanism. The cannula attachment device may be operable using a single hand when attaching and releasing the cannula. The attachment device may securely retain the cannula until a user actuates a release mechanism to disengage the cannula from the device; thus, the attachment device may prevent an accidental release of the cannula. The attachment device may require a minimal amount of force from a user to attach and release the cannula. For example, the attachment device may require a user to exert less than five pounds of force to attach and release the cannula.

The cam lock mechanism of the cannula attachment device may include a latch that automatically latches into the cannula when the cannula is inserted into a cavity or recess of the attachment device. The latch may be biased in its latched position (e.g., closed position) by a biasing element such as a torsion spring. A user may actuate a lever to move or rotate the latch to an open position such that a portion of the cannula can be inserted into the recess of the attachment device. The lever may be connected to the latch via a gear system, which acts as a force multiplier. For example, the gear system may allow a user to exert a force that is smaller than the force applied by the torsion spring in order to overcome the torsion spring force and move the latch. A user can exert a four-pound force on the lever, which may be multiplied by a gear system having a gear ratio of, for example, at least 1.5:1 in order to help the user overcome a six-pound torsion spring. When the cam lock mechanism has secured the cannula in place, the cannula attachment device is capable of resisting external forces acting on the cannula. For example, when the latch of the cam lock mechanism has latched onto the cannula, the latch may have a near over-axis alignment that reduces potential movement or rotation of the latch when a lateral pulling force is exerted on the cannula. The attachment device may be capable of resisting torsional, bending, and other forces applied to the attachment device.

In some variations, the attachment device may have sensing capabilities for sensing and/or identifying a trocar or cannula. For example, the attachment device may have a sensor that detects a position of the latch of the cam lock mechanism in order to determine whether the latch has latched onto a cannula or trocar. The sensor may be, for example, a transducer such as a Hall effect sensor which is capable of detecting a magnetic field. The Hall effect sensor may operate by detecting a location of a magnet disposed on a portion of the latch. As another example, the attachment device may have a sensor that determines a type of trocar or cannula that has been inserted into the attachment device. The sensor may be, for example, a magnetic pole or magnetic field sensor that is capable of identifying certain types of trocars or cannulas.

Figure 14:
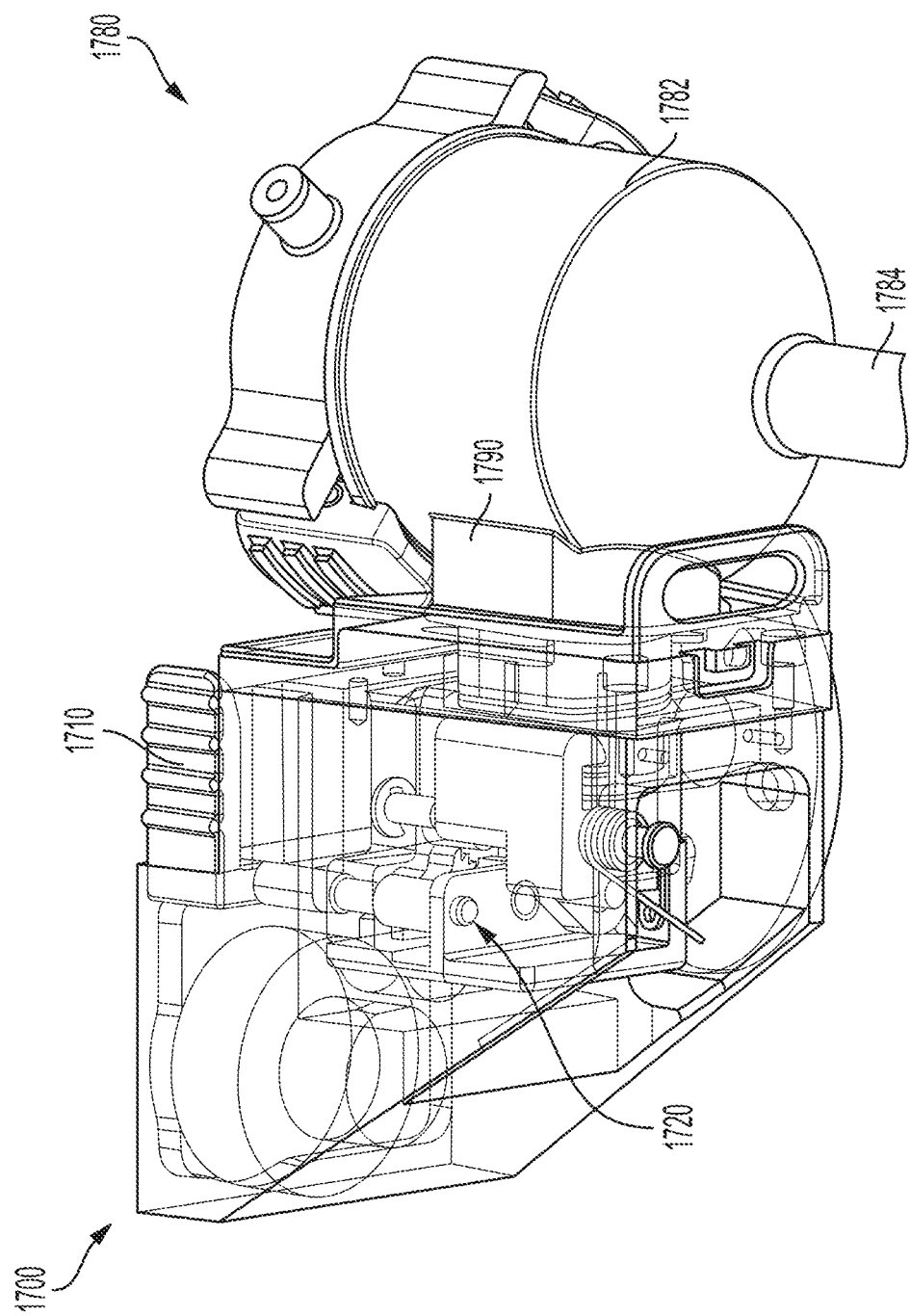
FIG. 14 is a schematic illustration of another exemplary variation of a cannula attachment device.
Figure 15A:
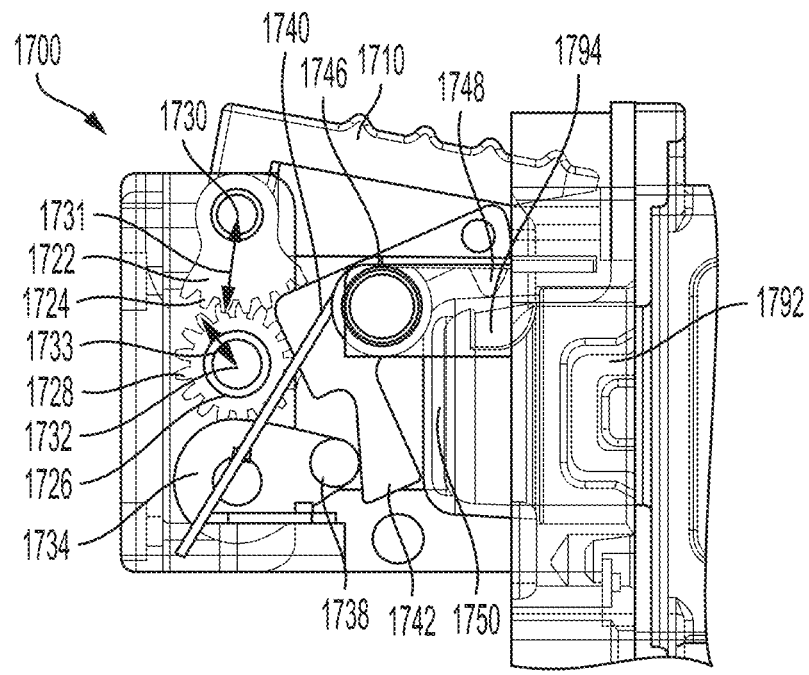
FIG. 15A is an enlarged view of an attachment region of the cannula attachment device depicted in FIG. 14 in a first configuration.
Figure 15B:
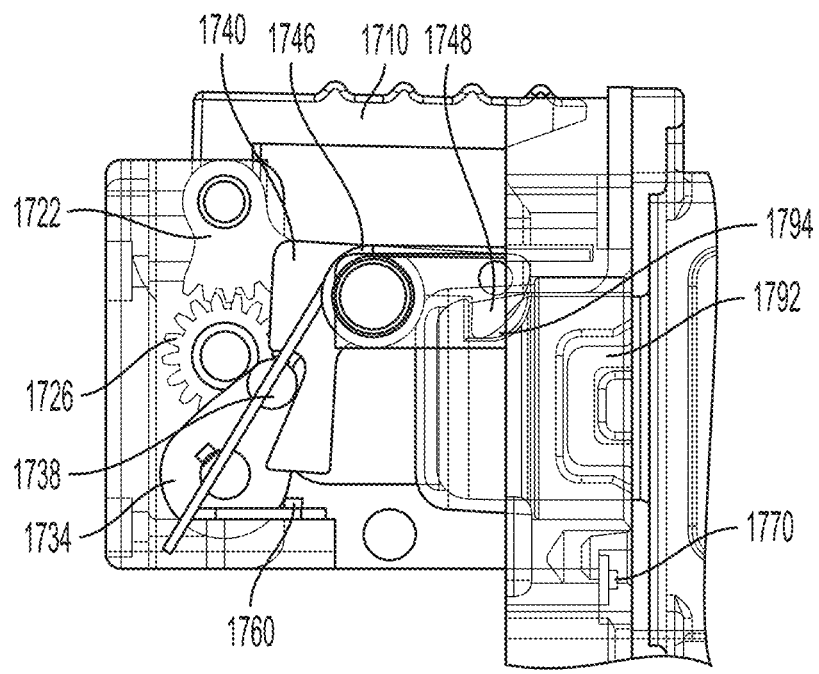
FIG. 15B is an enlarged view of the attachment region of the cannula attachment device depicted in FIG. 14 in a second configuration.

FIGS. 14-15B depict an exemplary variation of an attachment device for attaching a cannula, such as a cannula 1780, to a tool driver or robotic arm of a surgical table, where the attachment device includes a cam lock mechanism. FIG. 14 is a perspective view of the attachment device 1700, and FIGS. 15A-15B are enlarged views of a cam lock mechanism of attachment device 1700 in two different configurations. As shown in FIG. 14, the attachment device 1700 includes an actuating member, such as a lever 1710. The lever 1710 may be connected to a gear assembly 1720. When actuated, the lever 1710 may drive one or more gears of the gear assembly 1720 to move a locking member, such as a latch 1740, as depicted in FIGS. 15A-15B.

The cannula 1780 can be similar in structure and/or function to one or more other cannulas described herein. For example, the cannula 1780 may have a proximal portion 1782, such as, for example, a hub, fitting, connector, etc. The proximal portion 1782 of the cannula 1780 may include an attachment portion 1790. The attachment portion 1790 may extend from a side of the proximal portion 1782. The cannula 1780 may also have a shaft 1784 (partially depicted in FIG. 14) that extends distally from the proximal portion 1782.

The latch 1740 of the attachment device 1700 may be may be movable between a closed position, as shown in FIGS. 14 and 15B, and an open position, as shown in FIG. 15A. The latch 1740 may, for example, include a protrusion 1748 that is configured to latch into a correspondingly shaped recess 1794 formed in the attachment portion 1790 of the cannula 1780. Alternatively, the latch 1740 may include a recess that is configured to receive a correspondingly-shaped protrusion disposed on the attachment portion 1790 of the cannula 1780. When the protrusion 1748 is latched into the recess 1794, the latch 1740 may ensure that the attachment portion 1790 is securely attached to the tool driver or robotic arm of the surgical table. The latch 1740 may be biased to the closed position by a biasing element such as a spring 1746. When the latch 1740 is in the closed position, the protrusion 1748 of the latch 1740 may be disposed in a space or region 1750 of the attachment device 1700 in which the attachment portion 1790 can be inserted. But when the protrusion 1748 is disposed in the region 1750, the protrusion 1748 may substantially prevent the attachment portion 1790 from being inserted fully into the region 1750. For example, a surface of the protrusion 1748 may contact a leading surface of the attachment portion 1790 and prevent the attachment portion 1790 from being inserted further into the region 1750.

Accordingly, when attaching the cannula 1780 to the attachment device 1700, a user may need to move the latch 1740 to the open position, shown in FIG. 5A, such that the protrusion 1748 is not disposed in the region 1750 for receiving the attachment portion 1790 of the cannula 1780. The user may actuate the lever 1710, for example, by depressing the lever 1710, to move the latch 1740. Advantageously, the lever 1710 can be actuated by a user using one hand. The lever 1710 may drive movement of one or more gears and links of the gear assembly 1720 (e.g., gears 1722, 1726 and link 1734) to move the latch 1740. The biasing force of the spring 1746 must be overcome in order to allow the latch 1740 to move to the open position. But based on the relative sizes of the gears of the gear assembly 1720, which can be designed to act as a force multiplier with a suitable gear ratio, the force applied by the user can be less than the biasing force of the spring 1746 in order to overcome the spring biasing force and move the latch 1740 to the open position. For example, the lever 1710 can be attached to a first gear 1722. The first gear 1722 may have teeth 1724 that are disposed a distance 1731 from a center 1730 of the first gear 1722. The teeth 1724 of the first gear 1722 may be configured to engage with teeth 1728 of a second gear 1726. The teeth 1728 of the second gear 1726 may be disposed a distance 1733 from a center 1732 of the second gear 1726. When the distance 1731 is greater than the distance 1733, the two gears 1722, 1726 may act as a force multiplier, thereby allowing the user to apply less force to overcome the biasing force of the spring 1746. For example, the user may only need to apply a four-pound force in order to overcome a spring biasing force of six pounds, if the gear ratio between the first and second gears is about 1.5:1. In some variations, the two gears 1722, 1726 may be connected in series with one or more additional gears that may increase the effective gear ratio and force multiplying effect of the gear assembly 1720. The rotation of the two gears 1722, 1726 may drive movement of a link 1734. When the link 1734 moves to its position as shown in FIG. 15A, a portion 1738 of the link 1734 may engage with a portion 1742 of the latch 1740, thereby causing the latch 1740 to move to its open position.

Once the latch 1740 is in its open position, the user may insert the attachment portion 1790 of the cannula 1780 into the region 1750 of the attachment device 1700, as shown in FIG. 15A. The user may then release the lever 1710 to allow the spring 1746 to bias the latch 1740 back to its closed position, as shown in FIG. 15B. When the latch 1740 is biased back to its closed position, the protrusion 1748 of the latch may be disposed in the recess 1814 of the attachment portion 1790, securing the attachment portion 1790 in the region 1750 of the attachment device 1700. In the closed position, the latch 1740 may have a near over-axis or over-center alignment such that the latch 1740 may resist movement or rotation when a pulling force is exerted on the cannula 1780. In an exemplary variation, the attachment device may be designed to resist moments of up to 250 inch-pounds (in-lbs) and/or forces of up to 37 N.

The region 1750 may be shaped to correspond to a shape of the attachment portion 1790. In a variation, the region 1750 can be designed to accommodate a portion of the cannula 1780 (e.g., the attachment portion 1790) having a diameter of approximately 42 millimeters (mm), but in other variations, the attachment device may be modified to accommodate cannulas having larger or smaller diameters. In some variations, the attachment portion 17910 may have a cylindrical or an elliptical cross-sectional shape (e.g., an oval or elongated round shape). The elongated sides of an elliptical cross-sectional shape may, for example, help prevent rotation and translation of the cannula relative to the region 1750. In other variations, the attachment portion 1790 may be shaped differently (e.g., have a trapezoidal prism shape, square frustum shape, frusto-pyramidal shape, etc.), and the region 1750 may be correspondingly shaped to receive the attachment portion 1790. In some aspects, the region 1750 may be tapered (and the attachment portion 1790 may be correspondingly tapered) to facilitate easier insertion of the attachment portion 1790 into the region 1750.

The attachment device 1700 may include one or more sensors for sensing positions of other components of the attachment device 1700 and/or a type of trocar or cannula that has been inserted into the attachment device 1700. For example, a sensor 1760 may be positioned proximate to the portion 1742 of the latch 1740 and may detect when the latch 1740 is in its closed position and has latched onto a cannula. The sensor 1760 may be an optical sensor, magnetic sensor, or other type of sensor that provides a reading or electrical signal in response to a movement of the latch 1740. In some variations, the latch 1740 may include one or more magnets that may generate a magnetic field, which can be detected by the sensor 1760 to determine a position of the latch 1740, and to determine whether a trocar or cannula has been inserted into the attachment device 1700. In another example, the attachment device 1700 may have a sensor 1770 that is positioned proximate to a surface of a trocar or cannula, such as the cannula 1780, when the trocar or cannula is inserted into the attachment device 1700. Alternatively or additionally, the sensor 1770 may be an optical sensor, magnetic sensor, or other type of sensor that provides a reading or electrical signal in response to a presence of a trocar or cannula. The trocar or cannula may include magnets or other electrical components that may generate a magnetic field that can be detected by the sensor 1770 and used to detect whether the trocar or cannula has been properly placed and attached to the attachment device 1700 and/or a type of the trocar or cannula (e.g., whether the trocar or cannula is of a certain size, or configured to receive instruments of a certain type and size). Additionally or alternatively, the trocar or cannula may have a barcode or other type of identifying feature that can be detected (e.g., scanned, imaged) by the sensor 1770 to determine a type of the trocar or cannula.

In some variations, a sterile adapter element 1792 for separating the non-sterile attachment device 1700 from the sterile cannula 1780 may also include a drape or other sterile sheet (e.g., plastic) that fits between the non-sterile latch 1740 on the attachment device 1700 and the attachment portion 1790 of the cannula 1780. The sterile adapter element 17912 may be sufficiently flexible such that it can conform to a shape of the non-sterile latch 1740 and the attachment portion 1790 when the two are engaged with one another.

Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The invention claimed is:

1. An apparatus for attaching a cannula to a robotic surgical system, the apparatus comprising:
a support;
a first clamp component configured to pivot between an open position and a closed position;
a second clamp component spaced from the first clamp component, the first and second clamp components defining a region configured to receive a portion of the cannula, the first and second clamp components configured to retain the portion of the cannula in the region when the first clamp component is in the closed position;
a locking component pivotably coupled to the support and slidably coupled to the first clamp component, wherein the locking component is configured to pivot at the support to slide a portion of the locking component along the first clamp component from an unlocked position to a locked position; and
a locating structure disposed on at least one of the first clamp component and the second clamp component configured to mate with a corresponding structure disposed on the portion of the cannula.

2. The apparatus of claim 1, further comprising a sterile barrier configured to separate the first and second clamp components from the cannula when the portion of the cannula is received in the region.

3. The apparatus of claim 1, wherein the locked position is a locked over-center position in which the portion of the locking component is on an opposite side of a dead-center position from when the locking component is in the unlocked position.

4. The apparatus of claim 3, wherein the locking component is configured to lock the first clamp component in the closed position when the locking component is in the locked over-center position.

5. The apparatus of claim 3, wherein the first clamp component has a slot formed therein, the slot extending along a partial length of the first clamp component.

6. The apparatus of claim 5, wherein the locking component includes a first end and a second end, the first end including the portion of the locking component movable along a length of the slot formed in the first clamp component, the second end configured to be moved to pivot the locking component between the unlocked position and the locked over-center position.

7. The apparatus of claim 6, wherein the portion of the locking component moves in a first direction along the slot when the locking component pivots from the unlocked position to the locked over-center position, and wherein the portion of the locking component moves in a second direction along the slot opposite to the first direction when the locking component pivots from the locked over-center position to the unlocked position.

8. The apparatus of claim 1, wherein the locating structure includes at least one tapered surface configured to guide the portion of the cannula into the region between the first and second clamp components in a predefined orientation relative to the first and second clamp components.

9. The apparatus of claim 8, wherein the locating structure is configured to latch into the structure disposed on the portion of the cannula and retain the portion of the cannula within the region defined by the first and second clamp components when the first clamp component is in the closed position.

10. The apparatus of claim 8, wherein the locating structure includes two tapered surfaces forming a triangular protrusion.

11. The apparatus of claim 1, wherein the locating structure is frusto-pyramidal.

12. The apparatus of claim 1, further comprising a spring configured to bias the first clamp component in the closed position.

13. The apparatus of claim 1, wherein the support is further coupled to the second clamp component.

14. A method, comprising:
positioning a locking component of an attachment apparatus for a cannula in an unlocked position, wherein the locking component is pivotably coupled to a support and slidably coupled to a first clamp component and configured to pivot the first clamp component between an open position and a closed position, and wherein the first clamp component is positioned in the open position when the locking component is positioned in the unlocked position;
inserting a portion of the cannula into a region between the first clamp component and a second clamp component; and
pivoting the locking component at the support to slide a portion of the locking component along the first clamp component from the unlocked position to a locked position to pivot the first clamp component to the closed position, the first and second clamp components configured to retain the portion of the cannula in the region when the first clamp component is in the closed position.

15. The method of claim 14, wherein the locked position is a locked over-center position.

16. The method of claim 15, wherein the locking component is biased toward the locked over-center position when the locking component is in the locked over-center position.

17. The method of claim 15, wherein the locking component includes a first end and a second end, the first end including the portion of the locking component movable along a length of a slot formed in the first clamp component, the second end configured to be moved to pivot the locking component between the unlocked position and the locked position.

18. The method of claim 17, wherein the portion of the locking component moves in a first direction along the slot when the locking component pivots from the unlocked position to the locked position, and wherein the portion of the locking component moves in a second direction along the slot opposite to the first direction when the locking component pivots from the locked position to the unlocked position.

19. The method of claim 14, wherein the cannula is inserted into the region in a predefined orientation in which a locating structure disposed on at least one of the first clamp component and the second clamp component mates with a corresponding structure disposed on the portion of the cannula.

20. The method of claim 19, wherein the locating structure includes a first tapered surface and a second tapered surface, the first and the second tapered surfaces forming a triangular protrusion, and wherein the triangular protrusion is configured to latch into the portion of the cannula and retain the portion of the cannula within the region defined by the first and second clamp components when the first clamp component is in the closed position.

* * * * *